(12) United States Patent
Pozzi et al.

(10) Patent No.: US 11,433,069 B2
(45) Date of Patent: Sep. 6, 2022

(54) METHODS OF USE AND PHARMACEUTICAL COMBINATIONS COMPRISING HISTONE DEACETYLASE INHIBITORS AND JAK1/2 INHIBITORS

(71) Applicant: University of Modena and Reggio Emilia, Modena (IT)

(72) Inventors: Samantha Pozzi, Modena (IT); Maria Cosenza, Modena (IT); Monica Civallero, Modena (IT)

(73) Assignee: University of Modena and Reggio Emilia, Modena (IT)

( * ) Notice: Subject to any disclaimer, the term of this patent is extended or adjusted under 35 U.S.C. 154(b) by 0 days.

(21) Appl. No.: 16/768,439

(22) PCT Filed: Nov. 30, 2018

(86) PCT No.: PCT/IB2018/059540
§ 371 (c)(1),
(2) Date: May 29, 2020

(87) PCT Pub. No.: WO2019/106633
PCT Pub. Date: Jun. 6, 2019

(65) Prior Publication Data
US 2020/0383980 A1  Dec. 10, 2020

Related U.S. Application Data

(60) Provisional application No. 62/593,623, filed on Dec. 1, 2017.

(51) Int. Cl.
| | | |
|---|---|---|
| *A61K 31/505* | (2006.01) | |
| *A61P 35/02* | (2006.01) | |
| *A61K 31/5377* | (2006.01) | |

(52) U.S. Cl.
CPC ........ *A61K 31/505* (2013.01); *A61K 31/5377* (2013.01); *A61P 35/02* (2018.01)

(58) Field of Classification Search
CPC .... A61K 31/505; A61K 31/5377; A61P 35/02
USPC .................................................. 514/235.8
See application file for complete search history.

(56) References Cited

FOREIGN PATENT DOCUMENTS

| WO | WO 2011/091213 A2 | 7/2011 |
| WO | WO 2015/054099 A2 | 4/2015 |
| WO | WO 2017/184774 A1 | 10/2017 |
| WO | 2017196261 | * 11/2017 |
| WO | WO 2017/196261 A1 | 11/2017 |

OTHER PUBLICATIONS

Adams et al., "The Bcl-2 Protein Family: Arbiter of Cell Survival", Science, Aug. 28, 1998, vol. 281, No. 5381, pp. 1322-1326.
Amengual et al., "Mechanisms of Acquired Drug Resistance to the HDAC6 Selective Inhibitor Ricolinostat Reveals Rational Drug-Drug Combination with Ibrutinib", Clinical Cancer Research, Jun. 15, 2017, vol. 23, No. 12, pp. 3084-3096.
Bose et al., "Investigational histone deacetylase inhibitors (HDACi) in myeloproliferative neoplasms", Expert Opinion on Investigational Drugs, Dec. 1, 2016, vol. 25, No. 12, pp. 1393-1403.
Chou et al., "Quantitative analysis of dose-effect relationships: the combined effects of multiple drugs or enzyme inhibitors", Adv. Enzyme Regul., 1984, vol. 22, pp. 27-55.
Chou, "Theoretical basis, experimental design, and computerized simulation of synergism and antagonism in drug-combination studies", Pharmacological Reviews, 2006, vol. 58, No. 3, pp. 621-681.
Holford et al., "Understanding the dose-effect relationship: clinical application of pharmacokinetic-pharmacodynamic models", Clinical Pharmacokinetics, 1981, vol. 6, pp. 429-453.
International Preliminary Report on Patentability for PCT International Patent Application No. PCT/IB2018/059540, dated Jun. 2, 2020.
International Search Report and Written Opinion for PCT International Patent Application No. PCT/IB2018/059540, dated Mar. 15, 2019.
Mishima et al., "Ricolinostat (ACY-1215) induced inhibition of aggresome formation accelerates carfilzomib-induced multiple myeloma cell death", British Journal of Haematology, May 1, 2015, Vo. 169, No. 3, pp. 423-434.
Yang et al., "Design and Synthesis of Janus Kinase 2 (JAK2) and Histone Deacetlyase (HDAC) Bispecific Inhibitors Based on Pacritinib and Evidence of Dual Pathway Inhibition in Hematological Cell Lines", Journal of Medicinal Chemistry, Sep. 22, 2016, vol. 59, No. 18, pp. 8233-8262.

* cited by examiner

*Primary Examiner* — Kahsay Habte
(74) *Attorney, Agent, or Firm* — Lathrop GPM LLP; Brian Trinque

(57) ABSTRACT

The disclosure relates to pharmaceutical combinations comprising an HDAC6 selective inhibitor and a JAK1/2 inhibitor for the treatment of a cancer, such as a hematological cancer, in a subject in need thereof. Also provided herein are methods for treating a cancer in a subject in need thereof, comprising administering to the subject an effective amount of an HDAC6 selective inhibitor and a JAK1/2 inhibitor.

8 Claims, 19 Drawing Sheets

METHODS OF USE AND PHARMACEUTICAL COMBINATIONS COMPRISING HISTONE DEACETYLASE INHIBITORS AND JAK1/2 INHIBITORS

CROSS REFERENCE TO RELATED APPLICATION

This application claims the benefit of U.S. Provisional Application No. 62/593,623, filed Dec. 1, 2017. The contents of this application are incorporated herein by reference in its entirety.

BACKGROUND

Histone deacetylase (HDAC) inhibition can cause cancer cell growth arrest. However, pan-HDAC inhibition leads to significant adverse effects and an alternative HDAC inhibition profile is desirable.

HDAC6 is a Class IIb HDAC and is known to remove acetyl groups from many cellular proteins, including α-tubulin and HSP90. It has been reported that HSP90 hyperacetylation destabilizes its target proteins, including ER and EGFR. Inhibitors of HDAC6 have demonstrated anti-cancer proliferative activity in various cancer types. Blocking HDAC6 activity has been shown to cause cancer cell growth inhibition through various mechanisms.

Janus kinase (JAK) 1 and 2 are tyrosine kinase proteins, both of which promote cancer growth, specifically hematological malignancies. The JAK2/STAT3 signaling pathway is abnormally activated in hematological malignancies. JAK1/2 inhibitors can treat primary and secondary myelofibrosis. Further, HDAC6 has been reported to be overexpressed in primary and cultured multiple myeloma cells and B and T-cell lymphoma.

Due to the dose-limiting toxicities of current pan-selective HDAC inhibitors, there is an ongoing need for improved methods for the treatment of cancer.

SUMMARY

In order to provide alternative, efficacious and less toxic cancer treatments, provided herein are methods for the treatment of a cancer (e.g., hematological cancer). Also provided herein are pharmaceutical combinations comprising an HDAC inhibitor and a JAK1/2 inhibitor. The pharmaceutical combinations and methods disclosed herein are well tolerated and do not exhibit the dose-limiting toxicities of prior therapies.

In one aspect, provided herein are pharmaceutical combinations comprising a therapeutically effective amount of:

a) a compound of Formula I

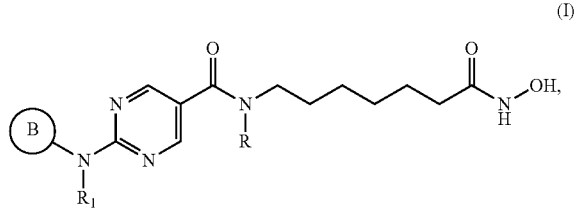

(I)

or a pharmaceutically acceptable salt thereof, wherein ring B is aryl or heteroaryl;

$R_1$ is aryl or heteroaryl, each of which may be optionally substituted by OH, halo, or $C_{1-6}$ alkyl;

and

R is H or $C_{1-6}$-alkyl; and b) a JAK1/2 inhibitor selected from the group consisting of momelotinib, baricitinib, filgotinib, gandotinib, lestaurtinib, pacritinib, ruxolitinib, tofacitinib, oclacitinib, and upadacitinib, or a pharmaceutically acceptable salt thereof.

In an embodiment of the pharmaceutical combinations, the compound of Formula I is Compound A

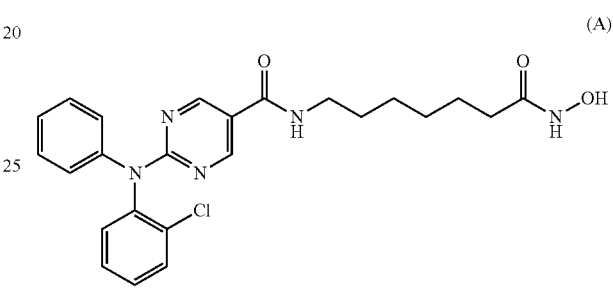

(A)

or a pharmaceutically acceptable salt thereof.

In another embodiment of the pharmaceutical combinations, the compound of Formula I is Compound B

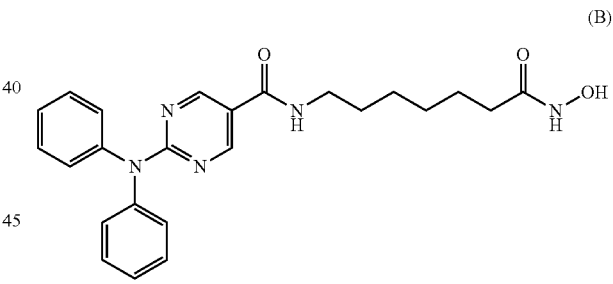

(B)

or a pharmaceutically acceptable salt thereof.

In another embodiment of the pharmaceutical combinations, the JAK1/2 inhibitor is momelotinib, or a pharmaceutically acceptable salt thereof.

In another embodiment of the pharmaceutical combinations, the combination is formulated in a single unit dosage form.

In an embodiment of the pharmaceutical combinations, the single unit dosage form further comprises one or more pharmaceutically acceptable carriers.

In another embodiment of the pharmaceutical combinations, the combination is formulated in separate unit dosage forms.

In another aspect, provided herein are methods of treating cancer in a subject in need thereof, comprising administering to the subject a therapeutically effective amount of:

a) a compound of Formula I

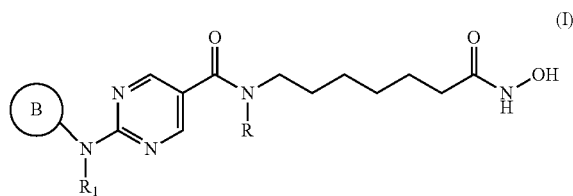

or a pharmaceutically acceptable salt thereof,
wherein
ring B is aryl or heteroaryl;
$R_1$ is aryl or heteroaryl, each of which may be optionally substituted by OH, halo, or $C_{1-6}$-alkyl; and
R is H or $C_{1-6}$alkyl; and
b) a JAK1/2 inhibitor selected from the group consisting of momelotinib, baricitinib, filgotinib, gandotinib, lestaurtinib, pacritinib, ruxolitinib, tofacitinib, ocacitinib, and upadacitinib, or a pharmaceutically acceptable salt thereof.

In an embodiment of the methods, the compound of Formula I is Compound A

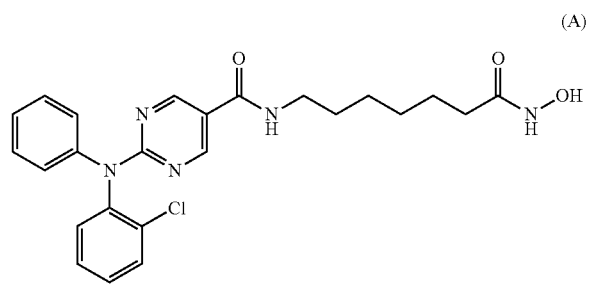 [SMILES: O=C(CCCCCCNC(=O)c1cnc(N(c2ccccc2)c2ccccc2Cl)nc1)NO]

or a pharmaceutically acceptable salt thereof.

In another embodiment of the methods, the compound of Formula I is Compound B

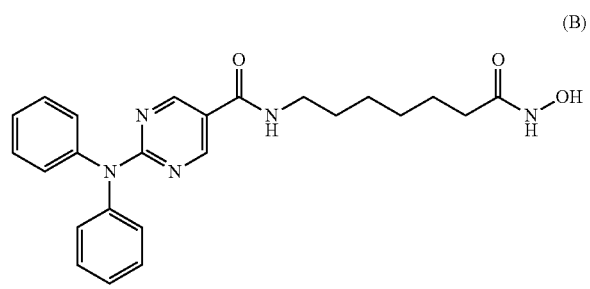 [SMILES: O=C(CCCCCCNC(=O)c1cnc(N(c2ccccc2)c2ccccc2)nc1)NO]

or a pharmaceutically acceptable salt thereof.

In another embodiment of the methods, the JAK1/2 inhibitor is momelotinib, or a pharmaceutically acceptable salt thereof.

In yet another embodiment of the methods, the compound of Formula I and the JAK1/2 inhibitor are formulated together as a single formulation.

In another embodiment of the methods, the compound of Formula I and the JAK1/2 inhibitor are each formulated as separate formulations.

In another embodiment of the methods, the compound of Formula I and the JAK1/2 inhibitor are administered at substantially the same time.

In yet another embodiment of the methods, the compound of Formula I and the JAK1/2 inhibitor are administered at different times.

In another embodiment of the methods, the cancer is a hematological cancer.

In another embodiment of the methods, the hematological cancer is selected from the group consisting of leukemia, lymphoma, and multiple myeloma.

In some embodiments of the pharmaceutical combinations disclosed herein, the combination further comprises one or more pharmaceutically acceptable carriers.

Also provided herein are uses of the pharmaceutical combinations disclosed herein for the manufacture of a pharmaceutical preparation or medicament for the treatment of cancer.

Other objects, features, and advantages will become apparent from the following detailed description. The detailed description and specific examples are given for illustration only because various changes and modifications within the spirit and scope of the disclosure will become apparent to those skilled in the art from this detailed description. Further, the examples demonstrate the principle of the disclosure.

BRIEF DESCRIPTION OF THE FIGURES

FIG. 4 shows that the combination of Compound A and momelotinib suppressed cell viability of lymphoid cell lines when co-cultured with bone marrow mesenchymal stromal cells (BM-MSCs).

FIG. 5 shows that the combination of Compound A and momelotinib affected the cell cycle.

FIG. 6 shows the effect of Compound A and momelotinib on apoptosis.

FIG. 8 shows that the combination of Compound A and momelotinib controls the signaling pathways of Bcl-2 family proteins and JAK2/STAT3. Lymphoma cell lines treated with 1 µM of momelotinib and 4 µM of citarinostat alone and in combination.

DETAILED DESCRIPTION

Figure 1:
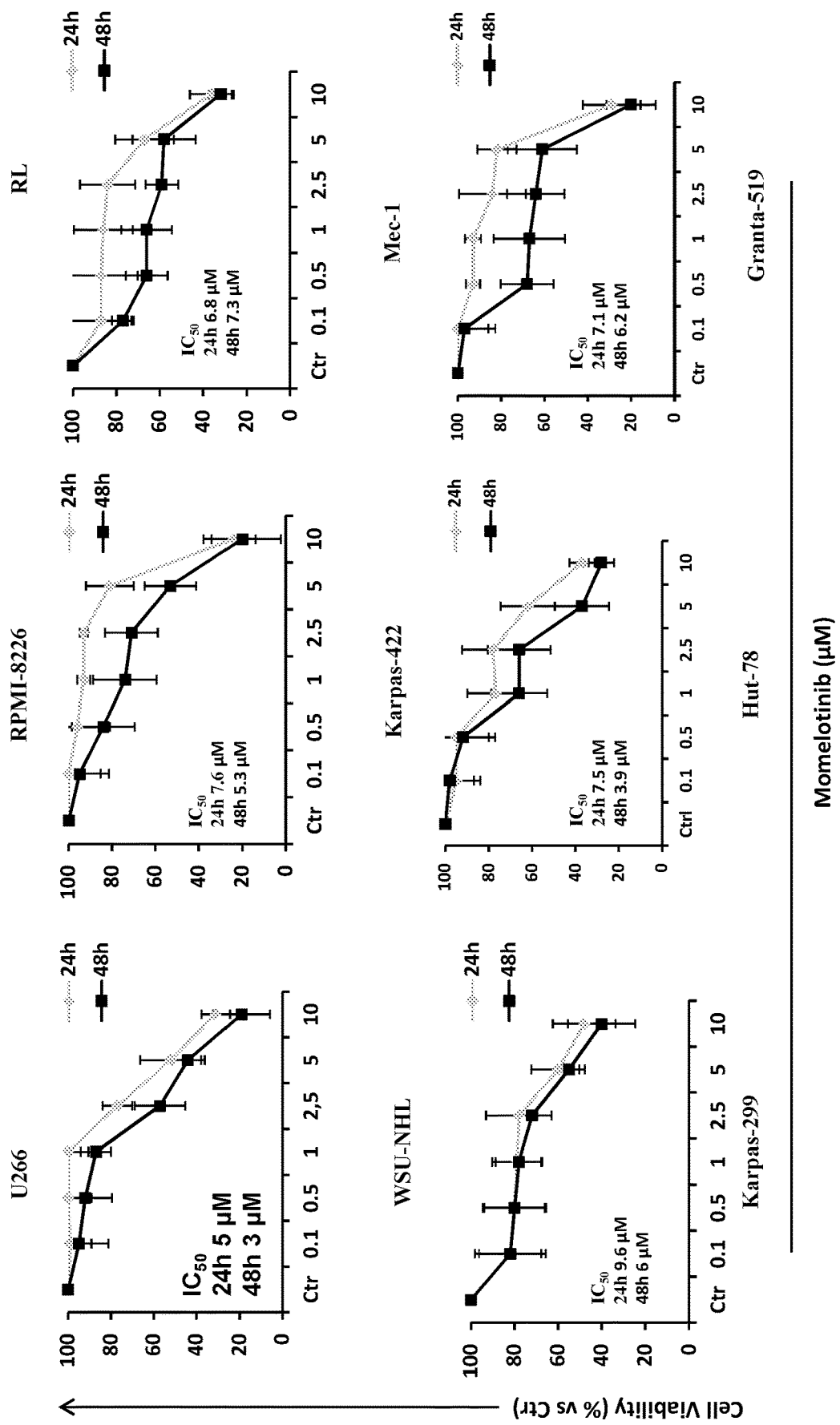
FIG. 1 shows that momelotinib decreases cell viability of hematological cancer cell lines. Line graphs show cell viability of 12 different hematological cancer cell fines following treatment with momelotinib at either 24 or 48 hours. The $IC_{50}$ of each cell line is noted in the graph. Data are representative of at least three independent experiments and represent the mean±SD.
Figure 1:
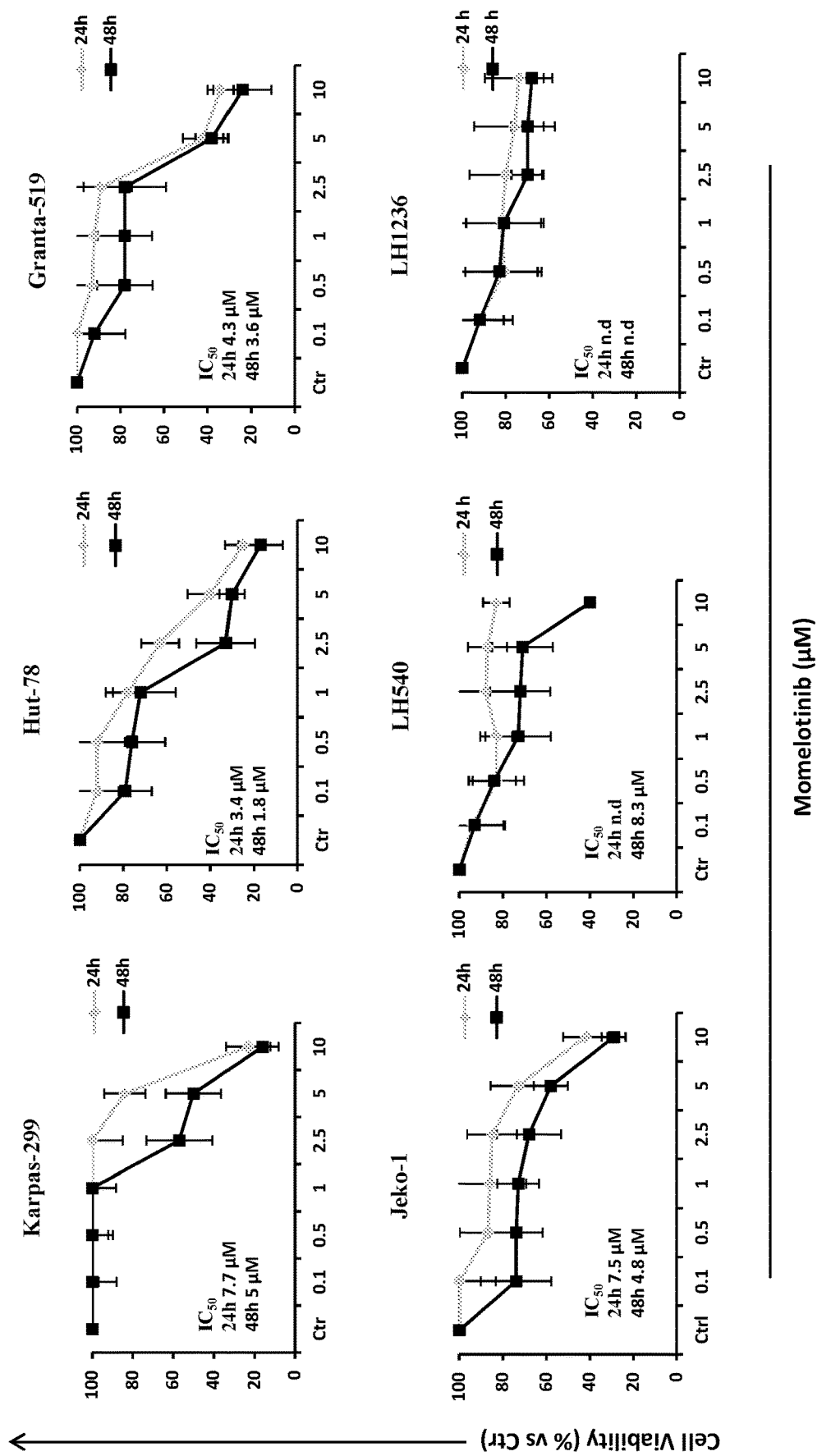

The present disclosure is directed to methods of using a histone deacetylase (HDAC) inhibitor and a JAK1/2 inhibitor for the treatment of a cancer. In particular, provided herein are methods for treating a hematological cancer in a patient in need thereof comprising administering a compound of Formula I and a JAK1/2 inhibitor. Also provided herein are combination products and pharmaceutical combinations comprising a compound of Formula I and a JAK1/2 inhibitor.

Definitions

Listed below are definitions of various terms used in this disclosure. These definitions apply to the terms as they are used throughout this specification and claims, unless otherwise limited in specific instances, either individually or as part of a larger group.

As used in the specification and in the claims, the term "comprising" may include the embodiments "consisting of" and "consisting essentially of." The terms "comprise(s)," "include(s)," "having," "has," "may," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated compounds, which allows the presence of only the named compounds, along with any pharmaceutically acceptable carriers, and excludes other compounds.

The term "about" generally indicates a possible variation of no more than 10%, 5%, or 1% of a value. For example, "about 25 mg/kg" will generally indicate, in its broadest sense, a value of 22.5-27.5 mg/kg, i.e., 25±2.5 mg/kg.

The term "alkyl" refers to saturated, straight- or branched-chain hydrocarbon moieties containing, in certain embodiments, between one and six, or one and eight carbon atoms, respectively. Examples of $C_{1-6}$-alkyl moieties include, but are not limited to, methyl, ethyl, propyl, isopropyl, n-butyl, tert-butyl, neopentyl, n-hexyl moieties; and examples of $C_{1-6}$-alkyl moieties include, but are not limited to, methyl, ethyl, propyl, isopropyl, n-butyl, tert-butyl, neopentyl, n-hexyl, heptyl, and octyl moieties.

The number of carbon atoms in an alkyl substituent can be indicated by the prefix "$C_{x-y}$," where x is the minimum and y is the maximum number of carbon atoms in the substituent. Likewise, a $C_x$ chain means an alkyl chain containing x carbon atoms.

The term "aryl" refers to a mono- or poly-cyclic carbocyclic ring system having one or more aromatic rings, fused or non-fused, including, but not limited to, phenyl, naphthyl, tetrahydronaphthyl, indanyl, idenyl, and the like. In an embodiment, $C_5$-$C_7$ aryl groups are provided herein.

The term "heteroaryl" refers to a mono- or poly-cyclic (e.g., bi-, or tri-cyclic or more) fused or non-fused, moiety or ring system having at least one aromatic ring, having from five to ten ring atoms of which one ring atom is selected from S, O, and N; zero, one or two ring atoms are additional heteroatoms independently selected from S, O, and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. In an embodiment, $C_4$-$C_7$ heteroaryl groups are provided herein.

The term "halo" refers to a halogen, such as fluorine, chlorine, bromine, and iodine.

The term "HDAC" refers to histone deacetylases, which are enzymes that remove the acetyl groups from the lysine residues in core histones, thus leading to the formation of a condensed and transcriptionally silenced chromatin. There are currently 18 known histone deacetylases, which are classified into four groups. Class I HDACs, which include HDAC1, HDAC2, HDAC3, and HDAC8, are related to the yeast RPD3 gene. Class II HDACs, which include HDAC4, HDAC5, HDAC6, HDAC7, HDAC9, and HDAC10, are related to the yeast Hda1 gene. Class III HDACs, which are also known as the sirtuins are related to the Sir2 gene and include SIRT1-7. Class IV HDACs, which contains only HDAC11, has features of both Class I and II HDACs. The term "HDAC" refers to any one or more of the 18 known histone deacetylases, unless otherwise specified.

The term "HDAC6 selective" means that the compound binds to HDAC6 to a substantially greater extent, such as 5×, 10×, 15×, 20× greater or more, than to any other type of HDAC enzyme, such as HDAC1 or HDAC2. That is, the compound is selective for HDAC6 over any other type of HDAC enzyme. For example, a compound that binds to HDAC6 with an $IC_{50}$ of 10 nM and to HDAC1 with an $IC_{50}$ of 50 nM is HDAC6 selective. On the other hand, a compound that binds to HDAC6 with an $IC_{50}$ of 50 nM and to HDAC1 with an $IC_{50}$ of 60 nM is not HDAC6 selective.

The term "inhibitor" is synonymous with the term antagonist.

A "JAK1/2 inhibitor" inhibits Janus kinase 1/2. A JAK inhibitor is able to reduce the activity of a JAK protein. In particular, a JAK1/2 inhibitor is able to reduce the activity of a JAK and/or a JAK2 protein. Reducing the activity of a protein may be direct or indirect—for example, by interfering with the expression of the protein or the mechanism by which the protein functions in a biological context. For example, the JAK or JAK2 kinase may require binding of a molecule of ATP to an ATP-binding site, so by specifically binding to and blocking the ATP-binding site, the activity of the JAK or JAK2 kinase is reduced. The activity of the JAK protein may also require the activity of another protein, such as a cytokine receptor, so interference with the activity of this protein may also reduce the activity of the JAK protein. Alternatively, fewer JAK or JAK2 kinase proteins may be expressed by interfering with gene expression at the relevant nucleic acid domain, such as the translation of the corresponding mRNA. For example, a JAK1/2 inhibitor includes, but is not limited to, momelotinib, baricitinib, filgotinib, gandotinib, lestaurtinib, pacritinib, ruxolitinib, tofacitinib, oclacitinib, and upadacitinib.

As used herein, the term "treatment" or "treating" indicates that the method has, at the least, mitigated the cancer. A method for treating comprises applying or administering to the subject a pharmaceutical combination comprising a compound of Formula I and a JAK1/2 inhibitor. A method for treating comprises applying or administering to an isolated tissue or cell line from a subject (e.g., for diagnosis or ex vivo applications), who has a cancer (e.g., a hematological cancer) a pharmaceutical combination comprising a compound of Formula I and a JAK1/2 inhibitor. The purpose of application or administration of the pharmaceutical combination is to treat, cure, heal, alleviate, relieve, after, remedy, ameliorate, improve or affect cancer. Such treatments may be specifically tailored or modified, based on knowledge obtained from the field of pharmacogenomics. The methods of the disclosure can, at the least, mitigate abnormal cellular proliferation. For example, the method can reduce the rate of cancer growth in a patient, or prevent the continued growth or spread of the cancer, or even reduce the overall reach of the cancer.

As used herein, the term "patient," "individual," or "subject" refers to a human or a non-human mammal. Non-human mammals include, for example, livestock and pets, such as ovine, bovine, porcine, canine, feline and murine mammals. Preferably, the patient, subject or individual is human.

As used herein, the term "hematological cancer" refers to forms of cancer that begin in cells of blood-forming tissues (e.g., bone marrow) or in the cells of the immune system (e.g., B cells). For example, a hematological cancer includes, but is not limited to, leukemia, lymphoma, and multiple myeloma. Leukemia includes, but is not limited to, acute myelogenous leukemia, acute lymphocytic leukemia, and chronic lymphocytic leukemia. Lymphoma includes but is not limited to B cell lymphoma, mantle cell lymphoma, cutaneous T cell lymphoma, anaplastic large cell lymphoma, and Non-Hodgkin's lymphoma.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure may be synthesized from the parent compound which contains a basic or acidic moiety by conventional chemical methods. Generally, such salts may be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art include, but are not limited to, intravenous, oral, aerosol, parenteral, ophthalmic, pulmonary and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient.

The term "combination," "therapeutic combination," "pharmaceutical combination," or "combination product" as used herein refer to either a fixed combination in one dosage unit form, or a non-fixed combination in separate dosage units, or a kit of parts for the combined administration where two or more therapeutic agents may be administered independently, at the same time, at substantially different times, or separately within time intervals, especially where these time intervals allow that the combination partners show a cooperative, e.g., synergistic, effect.

The term "combination therapy" refers to the administration of two or more therapeutic agents to treat a therapeutic condition or disorder described in the present disclosure. Such administration encompasses co-administration of these therapeutic agents in a substantially simultaneous manner, such as in a single formulation having a fixed ratio of active ingredients or in separate formulations (e.g., capsules and/or intravenous formulations) for each active ingredient. In addition, such administration also encompasses use of each type of therapeutic agent in a sequential or separate manner, either at approximately the same time or at different times. Such administration also encompasses each component being formulated as a separate formulation that can be administered at different times. For example, the JAK1/2 inhibitor can be dosed daily, every week, every 21 days, every 28 days, or every two months while the compound of Formula I can, for example, be dosed daily. In any case, the treatment regimen of the drug combination will provide beneficial effects in treating the conditions or disorders described herein.

The term "sub-therapeutically effective amount" or "sub-therapeutic dose" is an amount or dose of the active ingredient (e.g., a compound of Formula I or a JAK1/2 inhibitor), that, when administered to a patient by itself, does not completely inhibit over time the biological activity of the intended target.

The term "synergistic effect" refers to the action of two agents, such as, for example, an HDAC6 selective inhibitor compound of Formula I and a JAK1/2 inhibitor, producing an effect, for example, slowing the symptomatic progression of a cancer, such as, for example, a hematological cancer, or symptoms thereof, which is greater than the simple addition of the effects of each drug administered alone. A synergistic effect can be calculated, for example, using suitable methods such as the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984) and Chou, Pharmacol. Rev. 58: 621-681 (2006). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively. In some embodiments, the combinations described herein exhibit a synergistic effect (i.e., greater than additive effect) in the treatment of cancer. In further embodiments, the combinations described herein exhibit a synergistic effect (i.e., greater than additive effect) in the treatment of cancer.

As used herein, the term "resistant" or "refractive" to a therapeutic agent when referring to a cancer (e.g., a hematological malignancy) patient means that the cancer (e.g., hematological cancer) has innate or achieved resistance to, the effects of the therapeutic agent as a result of contact with the therapeutic agent. Stated alternatively, the cancer patient is resistant to the ordinary standard of care associated with the particular therapeutic agent.

As used herein, "treatment naïve" refers to the patient not having previously received treatment with a drug, either investigational or approved, for a cancer, such as a hematological cancer, in particular, a JAK1/2 inhibitor.

Alternatively, patients treated according to the methods of the disclosure may be "treatment experienced." As used herein, "treatment experienced" refers to a patient who has had at least one previous course of a cancer therapy, in particular a JAK1/2 inhibitor. In some embodiments, the last dose in this previous course occurred at least three months prior to implementing a method according to the present disclosure.

Histone Deacetylase (HDAC) Inhibitors

Provided herein are methods for treating a cancer in a subject in need thereof, comprising administering to the subject an HDAC inhibitor of Formula I and a JAK1/2 inhibitor. Also provided herein are pharmaceutical combinations comprising an HDAC inhibitor of Formula I and a JAK1/2 inhibitor.

The pharmaceutical combinations and methods disclosed herein comprise a histone deacetylase (HDAC) inhibitor of Formula I. The HDAC inhibitor may be any HDAC inhibitor. Thus, the HDAC inhibitor may be selective or non-selective to a particular type of histone deacetylase enzyme. Preferably, the HDAC inhibitor is a selective HDAC inhibitor. More preferably, the HDAC inhibitor is an HDAC6 selective inhibitor.

In some embodiments, the HDAC6 selective inhibitor is a compound of Formula I:

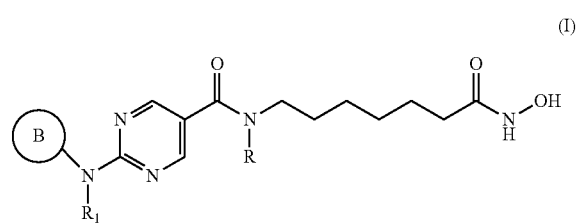

or a pharmaceutically acceptable salt thereof,
wherein
ring B is aryl or heteroaryl;
$R_1$ is an aryl or heteroaryl, each of which may be optionally substituted by OH, halo, or $C_{1-6}$alkyl;
and
R is H or $C_{1-6}$-alkyl.

In an embodiment of Formula I, $R_1$ is an aryl that is substituted by OH, halo, or $C_{1-6}$-alkyl.

In another embodiment of Formula I, $R_1$ is $C_5$-$C_7$ aryl that is substituted by OH, halo, or $C_{1-6}$-alkyl.

In another embodiment of Formula I, $R_1$ is $C_4$-$C_7$ heteroaryl that is substituted by OH, halo, or $C_{1-6}$-alkyl.

In yet another embodiment of Formula I, $R_1$ is phenyl that is substituted by OH, halo, or $C_{1-6}$-alkyl.

In yet another embodiment of Formula I, $R_1$ is phenyl that is substituted by chloro.

In yet another embodiment of Formula I, $R_1$ is phenyl that is substituted by halo.

In another embodiment of Formula I, ring B is $C_5$-$C_7$ aryl.

In another embodiment of Formula I, ring B is $C_4$-$C_7$ heteroaryl.

In yet another embodiment of Formula I, ring B is phenyl.

Representative compounds of Formula I include, but are not limited to:

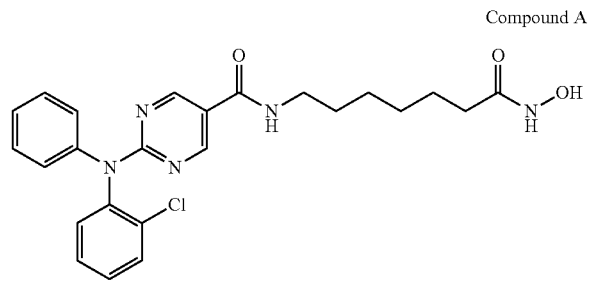

Compound A 2-((2-chlorophenyl)(phenyl)amino)-N-(7-(hydroxyamino)-7-oxoheptyl)pyrimidine-5-carboxamide $IC_{50}$(nM)  HDAC6 = 4  HDAC3 = 76

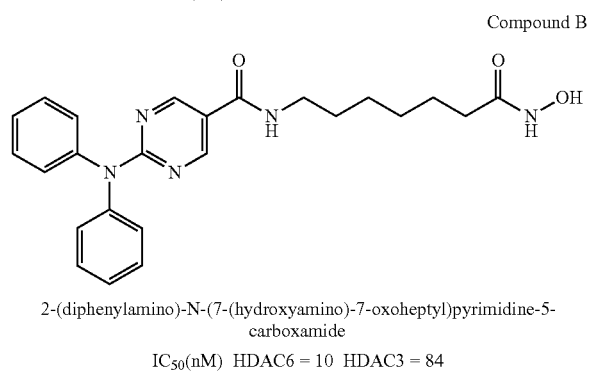

Compound B 2-(diphenylamino)-N-(7-(hydroxyamino)-7-oxoheptyl)pyrimidine-5-carboxamide $IC_{50}$(nM)  HDAC6 = 10  HDAC3 = 84 or pharmaceutically acceptable salts thereof. In some embodiments, the HDAC6 selective inhibitor is Compound A, or a pharmaceutically acceptable salt thereof. In other embodiments, the HDAC6 selective inhibitor is Compound B, or a pharmaceutically acceptable salt thereof.

The preparation and properties of selective HDAC6 inhibitors according to Formula I are provided in International Patent Application No. PCT/US2011/021982 and PCT/US2014/059238, the entire contents of which are incorporated herein by reference.

JAK1/2 Inhibitors

Some embodiments of the pharmaceutical combinations and methods disclosed herein comprise a JAK1/2 inhibitor. Examples of JAK1/2 inhibitors include, but are not limited to, momelotinib, baricitinib, filgotinib, gandotinib, lestaurtinib, pacritinib, ruxolitinib, tofacitinib, oclacitinib, and upadacitinib, or pharmaceutically acceptable salts thereof.

In some embodiments of the methods and the pharmaceutical combinations disclosed herein, the JAK1/2 inhibitor is selected from the group consisting of momelotinib, baricitinib, filgotinib, gandotinib, lestaurtinib, pacrtinib, ruxolitinib, tofacitinib, ocacitinib, and upadacitinib, or pharmaceutically acceptable salts thereof.

In some embodiments of the methods, the JAK1/2 inhibitor is momelotinib, or a pharmaceutically acceptable salt thereof. In some embodiments of the methods, the JAK1/2 inhibitor is baricitinib, or a pharmaceutically acceptable salt thereof. In other embodiments of the methods, the JAK1/2 inhibitor is filgotinib, or a pharmaceutically acceptable salt thereof. In some embodiments of the methods, the JAK1/2 inhibitor is gandotinib, or a pharmaceutically acceptable salt thereof. In other embodiments of the methods, the JAK1/2 inhibitor is lestaurtinib, or a pharmaceutically acceptable salt thereof. In other embodiments of the methods, the JAK1/2 inhibitor is pacritinib, or a pharmaceutically acceptable salt thereof. In yet other embodiments of the methods, the JAK1/2 inhibitor is upadacitinib, or a pharmaceutically acceptable salt thereof. In yet other embodiments of the methods, the JAK1/2 inhibitor is ruxolitinib, or a pharmaceutically acceptable salt thereof. In yet other embodiments of the methods, the JAK1/2 inhibitor is tofacitinib, or a pharmaceutically acceptable salt thereof. In yet other embodiments of the methods, the JAK1/2 inhibitor is oclacitinib, or a pharmaceutically acceptable salt thereof.

In some embodiments of the pharmaceutical combinations, the JAK1/2 inhibitor is momelotinib, or a pharmaceutically acceptable salt thereof. In some embodiments of the pharmaceutical combinations, the JAK1/2 inhibitor is baricitinib, or a pharmaceutically acceptable salt thereof. In other embodiments of the pharmaceutical combinations, the JAK1/2 inhibitor is filgotinib, or a pharmaceutically acceptable salt thereof. In some embodiments of the pharmaceutical combinations, the JAK1/2 inhibitor is gandotinib, or a pharmaceutically acceptable salt thereof. In other embodiments of the pharmaceutical combinations, the JAK1/2 inhibitor is lestaurtinib, or a pharmaceutically acceptable salt thereof. In other embodiments of the pharmaceutical combinations, the JAK1/2 inhibitor is pacritinib, or a pharmaceutically acceptable salt thereof. In yet other embodiments of the pharmaceutical combinations, the JAK1/2 inhibitor is upadacitinib, or a pharmaceutically acceptable salt thereof. In yet other embodiments of the pharmaceutical combinations, the JAK1/2 inhibitor is ruxolitinib, or a pharmaceutically acceptable salt thereof. In yet other embodiments of the pharmaceutical combinations, the JAK1/2 inhibitor is tofacitinib, or a pharmaceutically acceptable salt thereof. In yet other embodiments of the pharmaceutical combinations, the JAK1/2 inhibitor is oclacitinib, or a pharmaceutically acceptable salt thereof.

In some embodiments, the compounds described herein are unsolvated. In other embodiments, one or more of the compounds are in solvated form. As known in the art, the solvate can be any of pharmaceutically acceptable solvent, such as water, ethanol, and the like.

Although the compounds of Formula I are depicted in their neutral forms, in some embodiments, these compounds are used in a pharmaceutically acceptable salt form.

Pharmaceutical Combinations and Compositions

In an aspect, provided herein is a pharmaceutical combination comprising a histone deacetylase (HDAC) inhibitor of Formula I and a JAK1/2 inhibitor. In an embodiment, the HDAC inhibitor of is an HDAC6 selective inhibitor.

In an embodiment, the pharmaceutical combination comprises the HDAC inhibitor Compound A, or a pharmaceutically acceptable salt thereof, and a JAK1/2 inhibitor. In other embodiments, the pharmaceutical combination comprises the HDAC inhibitor Compound A, or a pharmaceutically acceptable salt thereof, and a JAK1/2 inhibitor, wherein the JAK1/2 inhibitor is selected from the group consisting of momelotinib, baricitinib, filgotinib, gandotinib, lestaurtinib, pacritinib, ruxolitinib, tofacitinib, oclacitinib, and upadacitinib, or pharmaceutically acceptable salts thereof. In another embodiment, the pharmaceutical combination comprises the HDAC inhibitor Compound A, or a pharmaceutically acceptable salt thereof, and the JAK1/2 inhibitor momelotinib, or a pharmaceutically acceptable salt thereof.

In yet another embodiment, the pharmaceutical combination comprises the HDAC inhibitor Compound B, or a pharmaceutically acceptable salt thereof, and a JAK1/2 inhibitor. In other embodiments, the pharmaceutical combination comprises the HDAC inhibitor Compound B, or a pharmaceutically acceptable salt thereof, and a JAK1/2 inhibitor, wherein the JAK1/2 inhibitor is selected from the group consisting of momelotinib, baricitinib, filgotinib, gandotinib, lestaurtinib, pacritinib, ruxolitinib, tofacitinib, oclacitinib, and upadacitinib, or pharmaceutically acceptable salts thereof. In another embodiment, the pharmaceutical combination comprises the HDAC inhibitor Compound B, or a pharmaceutically acceptable salt thereof, and the JAK1/2 inhibitor momelotinib, or a pharmaceutically acceptable salt thereof.

Also provided herein are uses of the foregoing pharmaceutical combinations and compositions for the manufacture of a pharmaceutical preparation or medicament for the treatment of a cancer. In an embodiment, the pharmaceutical combination is for use in the treatment of a cancer in a subject. In some embodiments, the cancer is a hematological cancer. In some embodiments, the hematological cancer is selected from the group consisting of leukemia, lymphoma, and multiple myeloma. In certain embodiments, the cancer is resistant or refractory to treatment with the JAK1/2 inhibitor.

In another embodiment, the pharmaceutical combination is for use in the treatment of cancer in a subject, wherein the subject is resistant or refractory to treatment with the JAK1/2 inhibitor.

In an embodiment, the pharmaceutical combination is for use in the treatment of a cancer in a subject, wherein the subject is treatment naïve.

Methods for Treating Cancer

In one aspect, the disclosure relates to methods for treating a cancer in a subject in need thereof, comprising administering to the subject a pharmaceutical combination of the disclosure. In some embodiments of the methods, the cancer is a hematological cancer. In some embodiments, the hematological cancer is selected from the group consisting of leukemia, lymphoma, and multiple myeloma. In other embodiments, the leukemia is selected from the group consisting of acute myelogenous leukemia, acute lymphocytic leukemia, and chronic lymphocytic leukemia. In other embodiments, the lymphoma is selected from the group consisting of B cell lymphoma, mantle cell lymphoma, cutaneous T cell lymphoma, anaplastic large cell lymphoma, and Non-Hodgkin's lymphoma.

Thus, provided herein are methods for treating a cancer in a subject in need thereof comprising administering to the subject a therapeutically effective amount of a pharmaceutical combination comprising an HDAC6 selective inhibitor of Formula I and a JAK1/2 inhibitor.

In one embodiment, provided herein is a method for treating a cancer in a subject in need thereof, comprising administering to the subject a therapeutically effective amount of an HDAC inhibitor of Formula I, or a pharmaceutically acceptable salt thereof, and a therapeutically effective amount of a JAK1/2 inhibitor. In some embodiments, provided herein is a method for treating a cancer in a subject in need thereof, comprising administering to the subject a therapeutically effective amount of Compound A, or a pharmaceutically acceptable salt thereof, and a therapeutically effective amount of a JAK1/2 inhibitor.

In another embodiment, provided herein is a method for treating a hematological cancer in a subject in need thereof, comprising administering to the subject a therapeutically effective amount of an HDAC inhibitor of Formula I, or a pharmaceutically acceptable salt thereof, and a therapeutically effective amount of a JAK1/2 inhibitor. In some embodiments, provided herein is a method for treating a hematological cancer in a subject in need thereof, comprising administering to the subject a therapeutically effective amount of Compound A, or a pharmaceutically acceptable salt thereof, and a therapeutically effective amount of a JAK1/2 inhibitor.

In another embodiment, provided herein is a method for treating a leukemia in a subject in need thereof, comprising administering to the subject a therapeutically effective amount of an HDAC inhibitor of Formula I, or a pharmaceutically acceptable salt thereof, and a therapeutically effective amount of a JAK1/2 inhibitor. In some embodiments, provided herein is a method for treating a leukemia in a subject in need thereof, comprising administering to the subject a therapeutically effective amount of Compound A, or a pharmaceutically acceptable salt thereof, and a therapeutically effective amount of a JAK1/2 inhibitor.

In another embodiment, provided herein is a method for treating a lymphoma in a subject in need thereof, comprising administering to the subject a therapeutically effective amount of an HDAC inhibitor of Formula I, or a pharmaceutically acceptable salt thereof, and a therapeutically effective amount of a JAK1/2 inhibitor. In some embodiments, provided herein is a method for treating a lymphoma in a subject in need thereof, comprising administering to the subject a therapeutically effective amount of Compound A, or a pharmaceutically acceptable salt thereof, and a therapeutically effective amount of a JAK1/2 inhibitor.

In another embodiment, provided herein is a method for treating a multiple myeloma in a subject in need thereof, comprising administering to the subject a therapeutically effective amount of an HDAC inhibitor of Formula I, or a pharmaceutically acceptable salt thereof, and a therapeutically effective amount of a JAK1/2 inhibitor. In some embodiments, provided herein is a method for treating a multiple myeloma in a subject in need thereof, comprising administering to the subject a therapeutically effective amount of Compound A. or a pharmaceutically acceptable salt thereof, and a therapeutically effective amount of a JAK1/2 inhibitor.

In another embodiment is a method for treating a cancer in a subject in need thereof, comprising administering to the subject a therapeutically effective amount of Compound A. or a pharmaceutically acceptable salt thereof, and a therapeutically effective amount of momelotinib, or a pharmaceutically acceptable salt thereof. This embodiment exhibits synergy such that sub-therapeutic amounts of Compound A or of momelotinib can be used in the method.

In another embodiment is a method for treating a hematological cancer in a subject in need thereof, comprising administering to the subject a therapeutically effective amount of Compound A, or a pharmaceutically acceptable salt thereof, and a therapeutically effective amount of momelotinib, or a pharmaceutically acceptable salt thereof.

In another embodiment is a method for treating a leukemia in a subject in need thereof, comprising administering to the subject a therapeutically effective amount of Compound A, or a pharmaceutically acceptable salt thereof, and a therapeutically effective amount of momelotinib, or a pharmaceutically acceptable salt thereof.

In another embodiment is a method for treating a lymphoma in a subject in need thereof, comprising administering to the subject a therapeutically effective amount of Compound A, or a pharmaceutically acceptable salt thereof, and a therapeutically effective amount of momelotinib, or a pharmaceutically acceptable salt thereof.

In another embodiment is a method for treating a multiple myeloma in a subject in need thereof, comprising administering to the subject a therapeutically effective amount of Compound A, or a pharmaceutically acceptable salt thereof, and a therapeutically effective amount of momelotinib, or a pharmaceutically acceptable salt thereof.

In yet another embodiment is a method for treating a cancer in a subject in need thereof, comprising administering to the subject a therapeutically effective amount of Compound A, or a pharmaceutically acceptable salt thereof, and a therapeutically effective amount of a JAK1/2 inhibitor selected from the group consisting of momelotinib, baricitinib, filgotinib, gandotinib, lestaurtinib, pacritinib, ruxolitinib, tofacitinib, oclacitinib, and upadacitinib, or pharmaceutically acceptable salts thereof.

In other embodiments, provided herein is a method for treating a cancer in a subject in need thereof, comprising administering to the subject a therapeutically effective amount of Compound B, or a pharmaceutically acceptable salt thereof, and a therapeutically effective amount of a JAK1/2 inhibitor. In some embodiments, the method comprises administering to the subject a therapeutically effective amount of Compound B, or a pharmaceutically acceptable salt thereof, and a therapeutically effective amount of the JAK1/2 inhibitor selected from the group consisting of momelotinib, baricitinib, filgotinib, gandotinib, lestaurtinib, pacritinib, ruxolitinib, tofacitinib, oclacitinib, and upadacitinib, or pharmaceutically acceptable salts thereof.

In another embodiment, provided herein is a method for treating a hematological cancer in a subject in need thereof, comprising administering to the subject a therapeutically effective amount of an HDAC inhibitor of Formula I, or a pharmaceutically acceptable salt thereof, and a therapeutically effective amount of a JAK1/2 inhibitor. In some embodiments, provided herein is a method for treating a hematological cancer in a subject in need thereof, comprising administering to the subject a therapeutically effective amount of Compound B, or a pharmaceutically acceptable salt thereof, and a therapeutically effective amount of a JAK1/2 inhibitor.

In another embodiment, provided herein is a method for treating a leukemia in a subject in need thereof, comprising administering to the subject a therapeutically effective amount of an HDAC inhibitor of Formula I, or a pharmaceutically acceptable salt thereof, and a therapeutically effective amount of a JAK1/2 inhibitor. In some embodiments, provided herein is a method for treating a leukemia in a subject in need thereof, comprising administering to the subject a therapeutically effective amount of Compound B, or a pharmaceutically acceptable salt thereof, and a therapeutically effective amount of a JAK1/2 inhibitor.

In another embodiment, provided herein is a method for treating a lymphoma in a subject in need thereof, comprising administering to the subject a therapeutically effective amount of an HDAC inhibitor of Formula I, or a pharmaceutically acceptable salt thereof, and a therapeutically effective amount of a JAK1/2 inhibitor. In some embodiments, provided herein is a method for treating a lymphoma in a subject in need thereof, comprising administering to the subject a therapeutically effective amount of Compound B, or a pharmaceutically acceptable salt thereof, and a therapeutically effective amount of a JAK1/2 inhibitor.

In another embodiment, provided herein is a method for treating a multiple myeloma in a subject in need thereof, comprising administering to the subject a therapeutically effective amount of an HDAC inhibitor of Formula I, or a pharmaceutically acceptable salt thereof, and a therapeutically effective amount of a JAK1/2 inhibitor. In some embodiments, provided herein is a method for treating a multiple myeloma in a subject in need thereof, comprising administering to the subject a therapeutically effective amount of Compound B, or a pharmaceutically acceptable salt thereof, and a therapeutically effective amount of a JAK1/2 inhibitor.

In another embodiment is a method for treating a cancer in a subject in need thereof, comprising administering to the subject a therapeutically effective amount of Compound B or a pharmaceutically acceptable salt thereof, and a therapeutically effective amount of momelotinib, or a pharmaceutically acceptable salt thereof. This embodiment exhibits synergy such that sub-therapeutic amounts of Compound B or of momelotinib can be used in the method.

In another embodiment is a method for treating a hematological cancer in a subject in need thereof, comprising administering to the subject a therapeutically effective amount of Compound B, or a pharmaceutically acceptable salt thereof, and a therapeutically effective amount of momelotinib, or a pharmaceutically acceptable salt thereof.

In another embodiment is a method for treating a leukemia in a subject in need thereof, comprising administering to the subject a therapeutically effective amount of Compound B, or a pharmaceutically acceptable salt thereof, and a therapeutically effective amount of momelotinib, or a pharmaceutically acceptable salt thereof.

In another embodiment is a method for treating a lymphoma in a subject in need thereof, comprising administering to the subject a therapeutically effective amount of Compound B, or a pharmaceutically acceptable salt thereof, and a therapeutically effective amount of momelotinib, or a pharmaceutically acceptable salt thereof.

In another embodiment is a method for treating a multiple myeloma in a subject in need thereof, comprising administering to the subject a therapeutically effective amount of Compound B, or a pharmaceutically acceptable salt thereof, and a therapeutically effective amount of momelotinib, or a pharmaceutically acceptable salt thereof.

In some embodiments of the foregoing methods, the cancer or the cancer cell is resistant or refractory to treatment with the JAK1/2 inhibitor. In another embodiment, the hematological cancer is resistant or refractory to treatment with the JAK1/2 inhibitor. In still another embodiment, the lymphoma is resistant or refractory to treatment with the JAK1/2 inhibitor. In yet another embodiment, the multiple myeloma is resistant or refractory to treatment with the JAK1/2 inhibitor. In yet another embodiment, the leukemia is resistant or refractory to treatment with the JAK1/2 inhibitor. In further embodiments of the methods disclosed herein, the cancer is resistant or refractory to treatment with a JAK1/2 inhibitor selected from the group consisting of momelotinib, baricitinib, filgotinib, gandotinib, lestaurtinib, pacritinib, ruxolitinib, tofacitinib, oclacitinib, and upadacitinib, or pharmaceutically acceptable salts thereof. In other embodiments of the methods disclosed herein, the cancer is resistant or refractory to treatment with momelotinib, or a pharmaceutically acceptable salt thereof.

The subject considered herein is typically a human. However, the subject can be any mammal for which treatment is desired. Thus, the methods described herein can be applied to both human and veterinary applications.

Administration/Dose

In an embodiment of the pharmaceutical combination, Compound A is in an amount from 600 mg to 3000 mg (e.g., about 600, about 800, about 1000, about 1200, about 1400, about 1600, about 1800, about 2000 mg). In a further embodiment of the pharmaceutical combination, Compound A is in an amount from 600 mg to 2000 mg. In a preferred embodiment of the pharmaceutical combination, Compound A is in an amount from 180 mg to 480 mg.

In another embodiment of the pharmaceutical combination, Compound A is in an amount from 5 mg to 600 mg (e.g., about 5, about 25, about 50, about 100, about 200, about 300, about 400, about 500, about 600 mg). In yet another embodiment of the pharmaceutical combination Compound A is 10 mg to 200 mg.

In an embodiment of the pharmaceutical combination, Compound B is in an amount from 600 mg to 3000 mg (e.g., about 600, about 800, about 1000, about 1200, about 1400, about 1600, about 1800, about 2000 mg). In a further embodiment of the pharmaceutical combination, Compound B is in an amount from 600 mg to 2000 mg. In a preferred embodiment of the pharmaceutical combination, Compound A is in an amount from 180 mg to 480 mg.

In another embodiment of the pharmaceutical combination, Compound B is in an amount from 5 mg to 600 mg (e.g., about 5, about 25, about 50, about 100, about 200, about 300, about 400, about 500, about 600 mg). In yet another embodiment of the pharmaceutical combination Compound B is 10 mg to 200 mg.

In an embodiment of the pharmaceutical combination, the JAK1/2 inhibitor is in an amount from 600 mg to 3000 mg (e.g., about 600, about 800, about 1000, about 1200, about 1400, about 1600, about 1800, about 2000 mg). In a further embodiment of the pharmaceutical combination, the JAK1/2 inhibitor is in an amount from 600 mg to 2000 mg.

In another embodiment of the pharmaceutical combination, the JAK1/2 inhibitor is in an amount from 5 mg to 600 mg (e.g., about 5, about 25, about 50, about 100, about 200, about 300, about 400, about 500, about 600 mg). In yet another embodiment of the pharmaceutical combination, the JAK1/2 inhibitor is 10 mg to 200 mg.

In an embodiment of the pharmaceutical combination, momelotinib is in an amount from 600 mg to 3000 mg (e.g., about 600, about 800, about 1000, about 1200, about 1400, about 1600, about 1800, about 2000 mg). In a further embodiment of the pharmaceutical combination, momelotinib is in an amount from 600 mg to 2000 mg. In a preferred embodiment of the pharmaceutical combination, momelotinib is in an amount from 150 mg to 300 mg.

In another embodiment of the pharmaceutical combination, momelotinib is in an amount from 5 mg to 600 mg (e.g., about 5, about 25, about 50, about 100, about 200, about 300, about 400, about 500, about 600 mg). In yet another embodiment of the pharmaceutical combination, momelotinib is 10 mg to 200 mg.

In an embodiment of the pharmaceutical combination, the ratio of the compound of Formula I to the JAK1/2 inhibitor is in the range of 700:1-1:40. In another embodiment, the ratio of the compound of Formula I to the JAK1/2 inhibitor is in the range of 2:1 to 1:2, for example, 2:1, 1:1, or 1:2; 170:1 to 150:1, for example, 170:1, 160:1 or 150:1; 3:1 to 1:1, for example, 3:1, 2:1 or 1:1; 4:1 to 1:1, for example, 4:1, 3:1, 2:1 or 1:1; or 30:1 to 10:1, for example, 30:1, 20:1 or 10:1.

In another embodiment of the pharmaceutical combination, the ratio of Compound A to the JAK1/2 inhibitor is in the range of 700:1-1:40. In another embodiment, the ratio of Compound A to the JAK1/2 inhibitor is in the range of 2:1 to 1:2, for example, 2:1, 1:1, or 1:2; 170:1 to 150:1, for example, 170:1, 160:1 or 150:1; 3:1 to 1:1, for example, 3:1, 2:1 or 1:1; 4:1 to 1:1, for example, 4:1, 3:1, 2:1 or 1:1; or 30:1 to 10:1, for example, 30:1, 20:1 or 10:1.

In another embodiment of the pharmaceutical combination, the ratio of Compound B to the JAK1/2 inhibitor is in the range of 700:1-1:40. In another embodiment, the ratio of Compound B to the JAK1/2 inhibitor is in the range of 2:1 to 1:2, for example, 2:1, 1:1, or 1:2; 170:1 to 150:1, for example, 170:1, 160:1 or 150:1; 3:1 to 1:1, for example, 3:1, 2:1 or 1:1; or 30:1 to 10:1, for example, 30:1, 20:1 or 10:1.

In another embodiment of the pharmaceutical combination, the ratio of Compound A to momelotinib is in the range of 700:1-1:40. In another embodiment, the ratio of Compound A to momelotinib is in the range of 2:1 to 1:2, for example, 2:1, 1:1, or 1:2; 170:1 to 150:1, for example, 170:1, 160:1 or 150:1; 3:1 to 1:1, for example, 3:1, 2:1 or 1:1; or 30:1 to 10:1, for example, 30:1, 20:1 or 10:1.

In some embodiments, the HDAC6 selective inhibitor (a compound of Formula I) is administered simultaneously with the JAK1/2 inhibitor. Simultaneous administration typically means that both compounds enter the patient at precisely the same time. However, simultaneous administration also includes the possibility that the HDAC6 selective inhibitor (a compound of Formula I) and the JAK1/2 inhibitor enter the patient at different times, but the difference in time is sufficiently miniscule that the first administered compound is not provided the time to take effect on the patient before entry of the second administered compound. Such delayed times typically correspond to less than 1 minute, and more typically, less than 30 seconds. In one example, wherein the compounds are in solution, simultaneous administration can be achieved by administering a solution containing the pharmaceutical combination of compounds. In another example, simultaneous administration of separate solutions, one of which contains the HDAC6 selective inhibitor (a compound of Formula I) and the other of which contains the JAK1/2 inhibitor, can be employed. In one example wherein the compounds are in solid form, simultaneous administration can be achieved by administering a composition containing the pharmaceutical combination of compounds. Alternatively, simultaneous administration can be achieved by administering two separate compositions, one comprising the HDAC6 selective inhibitor (a compound of Formula I) and the other comprising the JAK1/2 inhibitor.

In some embodiments, the pharmaceutical combination of compounds exhibits a synergistic effect (i.e., greater than additive effect) in the treatment of a cancer, such as a hematological cancer. The term "synergistic effect" refers to the action of two agents, such as, for example, a compound of Formula I and a JAK1/2 inhibitor, producing an effect, for example, slowing the symptomatic progression of cancer or symptoms thereof, which is greater than the simple addition of the effects of each drug administered by as single agents. A synergistic effect can be calculated, for example, using suitable methods such as the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively.

The compound of Formula I and the JAK1/2 inhibitor can be administered independently, at the same time or separately within time intervals, wherein these time intervals allow that the combination partners show a cooperative, e.g., synergistic, effect.

In an embodiment, when the compound of Formula I and the JAK1/2 inhibitor are not administered simultaneously, the two agents exhibit a synergistic effect. In some embodiments, the compound of Formula I is administered before the JAK1/2 inhibitor. In other embodiments, the JAK1/2 inhibitor is administered before the compound of Formula I. In other embodiments, the first administered compound is provided time to take effect on the patient before the second administered compound is administered. Generally, the difference in time does not extend beyond the time for the first administered compound to complete its effect in the patient, or beyond the time the first administered compound is completely or substantially eliminated or deactivated in the patient. In another embodiment, the compound of Formula I and the JAK1/2 inhibitor are administered at different times.

In some embodiments, the compound of Formula I and the JAK1/2 inhibitor are together formulated as a single formulation.

In other embodiments of the single formulation of the pharmaceutical combinations and compositions, the pharmaceutical combination or composition further comprises one or more pharmaceutically acceptable carriers.

In other embodiments, the compound of Formula I and the JAK1/2 inhibitor are each formulated as separate formulations.

In some embodiments, one or both of the compound of Formula I and the JAK1/2 inhibitor are administered in a therapeutically effective amount or dosage. A "therapeutically effective amount" is an amount of a compound of Formula I or of a JAK1/2 inhibitor that, when administered to a patient by itself, effectively treats cancer. An amount that proves to be a "therapeutically effective amount" in a given instance, for a particular subject, may not be effective for 100% of subjects similarly treated for the disease or condition under consideration, even though such dosage is deemed a "therapeutically effective amount" by skilled practitioners. The amount of the compound that corresponds to a therapeutically effective amount is strongly dependent on the type of cancer, stage of the cancer, the age of the patient being treated, and other facts. In general, therapeutically effective amounts of these compounds are well-known in the art, such as provided in the supporting references cited above.

In other embodiments, one or both of the compound of Formula I and the JAK1/2 inhibitor are administered in a sub-therapeutically effective amount or dosage. A sub-therapeutically effective amount is an amount of a compound of Formula I or a JAK1/2 inhibitor that, when administered to a patient by itself, does not completely inhibit overtime the biological activity of the intended target.

Thus, in one embodiment, a compound of Formula I or a JAK1/2 inhibitor are administered in an amount that would not be effective when one or both of the compounds of Formula I and the JAK1/2 inhibitor is administered alone, but which amounts are effective in combination.

Whether administered in therapeutic or sub-therapeutic amounts, the pharmaceutical combination of the compound of Formula I and the JAK1/2 inhibitor should be effective in treating cancer. For example, a sub-therapeutic amount of a compound of the JAK1/2 inhibitor can be an effective amount if, when combined with a compound of Formula I (HDAC6 selective inhibitor), the pharmaceutical combination is effective in the treatment of cancer.

In certain embodiments of the disclosure, the pharmaceutical combinations and methods include a compound of Formula I and a JAK1/2 inhibitor. Thus, in one embodiment, the pharmaceutical combinations and methods include Compound A, or a pharmaceutically acceptable salt thereof, and a JAK1/2 inhibitor. In another embodiment, the pharmaceutical combinations and methods include Compound B, or a pharmaceutically acceptable salt thereof, and a JAK1/2 inhibitor. These embodiments exhibit synergy such that sub-therapeutic amounts of the HDAC6 selective inhibitor or of the JAK1/2 inhibitor may be used. In certain embodiments of the disclosure, the pharmaceutical combinations and methods include an HDAC6 selective inhibitor (Compound A or Compound B) and a JAK1/2 inhibitor.

In different embodiments, depending on the pharmaceutical combination and the effective amounts used, the pharmaceutical combination of compounds can inhibit cancer growth, achieve cancer stasis, or even achieve substantial or complete cancer regression.

While the amounts of a compound of Formula I and a JAK1/2 inhibitor should result in the effective treatment of cancer, the amounts, when combined, are preferably not excessively toxic to the patient (i.e., the amounts are preferably within toxicity limits as established by medical guidelines). In some embodiments, either to prevent excessive toxicity and/or provide a more efficacious treatment of cancer, a limitation on the total administered dosage is provided. Typically, the amounts considered herein are per day; however, half-day and two-day or three-day cycles also are considered herein.

Different dosage regimens can be used to treat cancer. In some embodiments, a daily dosage, such as any of the exemplary dosages described above, is administered once, twice, three times, or four times a day for three, four, five, six, seven, eight, nine, or ten days. Depending on the stage and severity of the cancer, a shorter treatment time (e.g., up to five days) may be employed along with a high dosage, or a longer treatment time (e.g., ten or more days, or weeks, or months, or longer) may be employed along with a low dosage. For example, the JAK1/2 inhibitor can be dosed every week, every 21 days, every 28 days, every two months, every 16 weeks, or every 24 weeks. In some embodiments, a once- or twice-daily dosage is administered every other day. In some embodiments, each dosage contains both a compound of Formula I and a JAK1/2 inhibitor to be delivered as a single dosage, while in other embodiments, each dosage contains either a compound of Formula I and a JAK1/2 inhibitor to be delivered as separate dosages.

The compounds of Formula I, the JAK1/2 inhibitors, or their pharmaceutically acceptable salts or solvate forms, in pure form or in an appropriate pharmaceutical composition, can be administered via any of the accepted modes of administration or agents known in the art. The compounds can be administered, for example, orally, nasally, parenterally (intravenous, intramuscular, or subcutaneous), topically, transdermally, intravaginally, intravesically, intracisternally, or rectally. The dosage form can be, for example, a solid, semi-solid, lyophilized powder, or liquid dosage forms, such as for example, tablets, pills, soft elastic or hard gelatin capsules, powders, solutions, suspensions, suppositories, aerosols, or the like, preferably in unit dosage forms suitable for simple administration of precise dosages. A particular route of administration is oral, particularly one in which a convenient daily dosage regimen can be adjusted according to the degree of severity of the disease to be treated.

As discussed above, the compound of Formula I and the JAK1/2 inhibitor of the pharmaceutical combination can be administered in a single unit dose or separate dosage forms. Accordingly, the phrase "pharmaceutical combination" includes a combination of two drugs in either a single dosage form or separate dosage forms, i.e., the pharmaceutically acceptable carriers and excipients described throughout the application can be combined with a compound of Formula I and a JAK1/2 inhibitor in a single unit dose, as well as individually combined with a compound of Formula I and a JAK1/2 inhibitor when these compounds are administered separately.

Auxiliary and adjuvant agents may include, for example, preserving, wetting, suspending, sweetening, flavoring, perfuming, emulsifying, and dispensing agents. Prevention of the action of microorganisms is generally provided by various antibacterial and antifungal agents. Isotonic agents may also be included. Prolonged absorption of an injectable pharmaceutical form can be brought about by the use of agents delaying absorption. The auxiliary agents also can include wetting agents, emulsifying agents, pH buffering agents, and antioxidants.

Solid dosage forms can be prepared with coatings and shells, such as enteric coatings and others well-known in the art. They can contain pacifying agents and can be of such composition that they release the active compound or compounds in a certain part of the intestinal tract in a delayed manner. Examples of embedded compositions that can be used are polymeric substances and waxes. The active compounds also can be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., the compound of Formula I or JAK1/2 inhibitor described herein, or a pharmaceutically acceptable salt thereof, and optional pharmaceutical adjuvants in a carrier to thereby form a solution or suspension.

Generally, depending on the intended mode of administration, the pharmaceutically acceptable compositions will contain about 1% to about 99% by weight of the compounds described herein, or a pharmaceutically acceptable salt thereof, and 99% to 1% by weight of a pharmaceutically acceptable excipient. In one example, the composition will be between about 5% and about 75% by weight of a compound described herein, or a pharmaceutically acceptable salt thereof, with the rest being suitable pharmaceutical excipients.

Actual methods of preparing such dosage forms are known, or will be apparent, to those skilled in this art. Reference is made, for example, to Remington's Pharmaceutical Sciences, 18th Ed. (Mack Publishing Company, Easton, Pa., 1990).

Kits

In other embodiments, kits are provided. Kits according to the disclosure include package(s) comprising compounds or compositions of the disclosure. In some embodiments, kits comprise an HDAC6 selective inhibitor (compound of Formula I), or a pharmaceutically acceptable salt thereof, and a JAK1/2 inhibitor.

The phrase "package" means any vessel containing compounds or compositions presented herein. In some embodiments, the package can be a box or wrapping. Packaging materials for use in packaging pharmaceutical products are well-known to those of skill in the art. Examples of pharmaceutical packaging materials include, but are not limited to, bottles, tubes, inhalers, pumps, bags, vials, containers, syringes, bottles, and any packaging material suitable for a selected formulation and intended mode of administration and treatment.

The kit can also contain items that are not contained within the package, but are attached to the outside of the package, for example, pipettes.

Kits can further contain instructions for administering compounds or compositions of the disclosure to a patient. Kits also can comprise instructions for approved uses of compounds herein by regulatory agencies, such as the United States Food and Drug Administration. Kits can also contain labeling or product inserts for the compounds. The package(s) and/or any product insert(s) may themselves be approved by regulatory agencies. The kits can include compounds in the solid phase or in a liquid phase (such as buffers provided) in a package. The kits can also include buffers for preparing solutions for conducting the methods, and pipettes for transferring liquids from one container to another.

EXAMPLES

Examples have been set forth below for the purpose of illustration and to describe certain specific embodiments. However, the scope of the claims is not to be in any way limited by the examples set forth herein. Various changes and modifications to the disclosed embodiments will be apparent to those skilled in the art and such changes and modifications including, without limitation, those relating to the chemical structures, substituents, derivatives, formulations and/or methods of the disclosure may be made without departing from the spirit of the disclosure and the scope of the appended claims. Definitions of the variables in the structures in the schemes herein are commensurate with those of corresponding positions in the formulae presented herein.

The synthesis of the compounds of Formula I is provided in International Patent Application Nos. PCT/US2011/021982 (Compound A) and PCT/US2014/059238 (Compounds A and B), which are incorporated herein by reference in their entireties.

Example 1: Synthesis of 2-((2-chlorophenyl)(phenyl)amino)-N-(7-(hydroxyamino)-7-oxoheptyl)pyrimidine-5-carboxamide (Compound A)

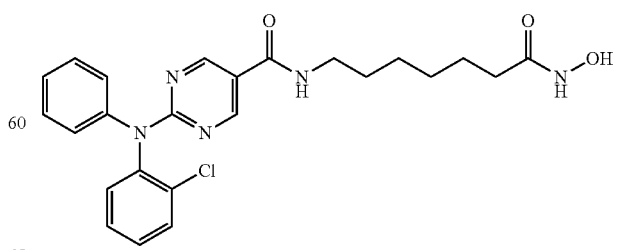

Reaction Scheme

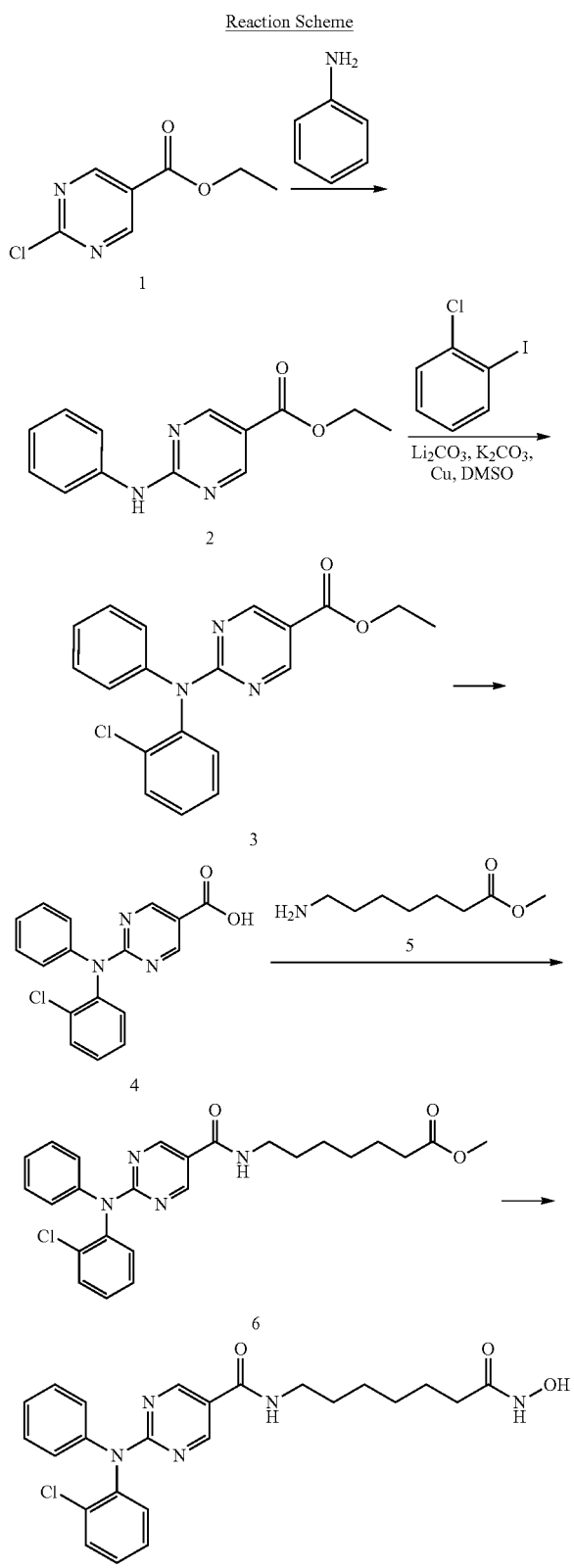

Synthesis of Intermediate 2:

A mixture of aniline (3.7 g, 40 mmol), compound 1 (7.5 g, 40 mmol), and K$_2$CO$_3$ (11 g, 80 mmol) in DMF (100 ml) was degassed and stirred at 120° C. under N$_2$ overnight. The reaction mixture was cooled to r.t. and diluted with EtOAc (200 ml), then washed with saturated brine (200 ml×3). The organic layers were separated and dried over Na$_2$SO$_4$, evaporated to dryness and purified by silica gel chromatography (petroleum ethers/EtOAc=10/1) to give the desired product as a white solid (6.2 g, 64%).

Synthesis of Intermediate 3:

A mixture of compound 2 (69.2 g, 1 equiv.), 1-chloro-2-iodobenzene (135.7 g, 2 equiv.), Li$_2$CO$_3$ (42.04 g, 2 equiv.), K$_2$CO$_3$ (39.32 g, 1 equiv.), Cu (1 equiv. 45 μm) in DMSO (690 ml) was degassed and purged with nitrogen. The resulting mixture was stirred at 140° C. Work-up of the reaction gave compound 3 at 93% yield.

Synthesis of Intermediate 4:

2N NaOH (200 ml) was added to a solution of compound 3 (3.0 g, 9.4 mmol) in EtOH (200 ml). The mixture was stirred at 60° C. for 30 min. After evaporation of the solvent, the solution was neutralized with 2N HCl to give a white precipitate. The suspension was extracted with EtOAc (2×200 ml), and the organic layers were separated, washed with water (2×100 ml), brine (2×100 ml), and dried over Na$_2$SO$_4$. Removal of the solvent gave a brown solid (2.5 g, 92%).

Synthesis of Intermediate 6:

A mixture of compound 4 (2.5 g, 8.58 mmol), compound 5 (2.52 g, 12.87 mmol), HATU (3.91 g, 10.30 mmol), and DIPEA (4.43 g, 34.32 mmol) was stirred at r.t. overnight. After the reaction mixture was filtered, the filtrate was evaporated to dryness and the residue was purified by silica gel chromatography (petroleum ethers/EtOAc=2/1) to give a brown solid (2 g, 54%).

Synthesis of 2-((2-chlorophenyl)(phenyl)amino)-N-(7-(hydroxyamino)-7-oxoheptyl)pyrimidine-5-carboxamide (Compound A)

A mixture of the compound 6 (2.0 g, 4.6 mmol), sodium hydroxide (2N, 20 mL) in MeOH (50 ml) and DCM (25 ml) was stirred at 0° C. for 10 min. Hydroxylamine (50%) (10 ml) was cooled to 0° C. and added to the mixture. The resulting mixture was stirred at r.t. for 20 min. After removal of the solvent, the mixture was neutralized with 1M HCl to give a white precipitate. The crude product was filtered and purified by pre-HPLC to give a white solid (950 mg, 48%).

Example 2: Synthesis of 2-(diphenylamino)-N-(7-(hydroxyamino)-7-oxoheptyl) pyrimidine-5-carboxamide (Compound B)

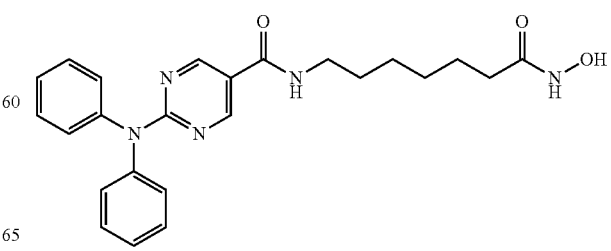

Reaction Scheme

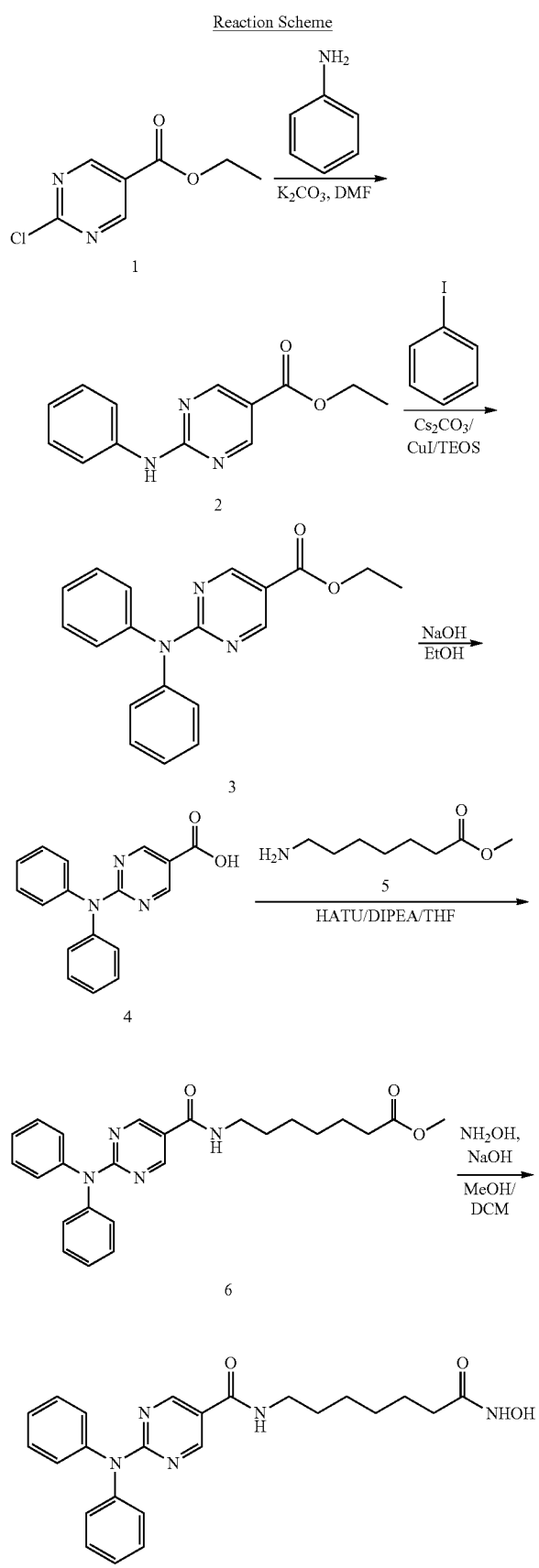

Synthesis of Intermediate 2:
See synthesis of intermediate 2 in Example 1.

Synthesis of Intermediate 3:

A mixture of compound 2 (6.2 g, 25 mmol), iodobenzene (6.12 g, 30 mmol), CuI (955 mg, 5.0 mmol), $Cs_2CO_3$ (16.3 g, 50 mmol) in TEOS (200 m) was degassed and purged with nitrogen. The resulting mixture was stirred at 140° C. for 14 hrs. After cooling to r.t., the residue was diluted with EtOAc (200 m). 95% EtOH (200 m) and $NH_4F$—$H_2O$ on silica gel [50 g, pre-prepared by the addition of $NH_4F$ (100 g) in water (1500 ml) to silica gel (500 g, 100-200 mesh)] was added, and the resulting mixture was kept at r.t. for 2 hrs. The solidified materials were filtered and washed with EtOAc. The filtrate was evaporated to dryness and the residue was purified by silica gel chromatography (petroleum ethers/EtOAc=10/1) to give a yellow solid (3 g, 38%).

Synthesis of Intermediate 4:
See synthesis of intermediate 4 in Example 1.

Synthesis of Intermediate 6:
See synthesis of intermediate 6 in Example 1.

Synthesis of 2-(diphenylamino)-N-(7-(hydroxyamino)-7-oxoheptyl)pyrimidine-5-carboxamide (Compound B)

See synthesis of Compound A in Example 1.

Example 3: HDAC Enzyme Assays

Compounds for testing were diluted in DMSO to 50 fold the final concentration and a ten point three fold dilution series was made. The compounds were diluted in assay buffer (50 mM HEPES, pH 7.4, 100 mM KCl, 0.001% Tween-20, 0.05% BSA, 20 µM Tris (2-carboxyethyl) phosphine) to 6 fold their final concentration. The HDAC enzymes (purchased from BPS Biosciences) were diluted to 1.5 fold their final concentration in assay buffer. The dipeptide substrate and trypsin at 0.05 µM final concentration were diluted in assay buffer at 6 fold their final concentration. The final enzyme concentrations used in these assays were 3.3 ng/ml (HDAC1), 0.2 ng/ml (HDAC2), 0.08 ng/ml (HDAC3) and 2 ng/ml (HDAC6). The final substrate concentrations used were 16 µM (HDAC1), 10 µM (HDAC2), 17 µM (HDAC3) and 14 µM (HDAC6). Five µl of compound and 20 µl of enzyme were added to wells of a black, opaque 384 well plate in duplicate. Enzyme and compound were incubated together at room temperature for 10 min. Five µl of substrate was added to each well, the plate was shaken for 60 seconds and placed into a Victor 2 microliter plate reader. The development of fluorescence was monitored for 60 min. and the linear rate of the reaction was calculated. The $IC_{50}$ was determined using Graph Pad Prism by a four parameter curve fit.

Figure 2:
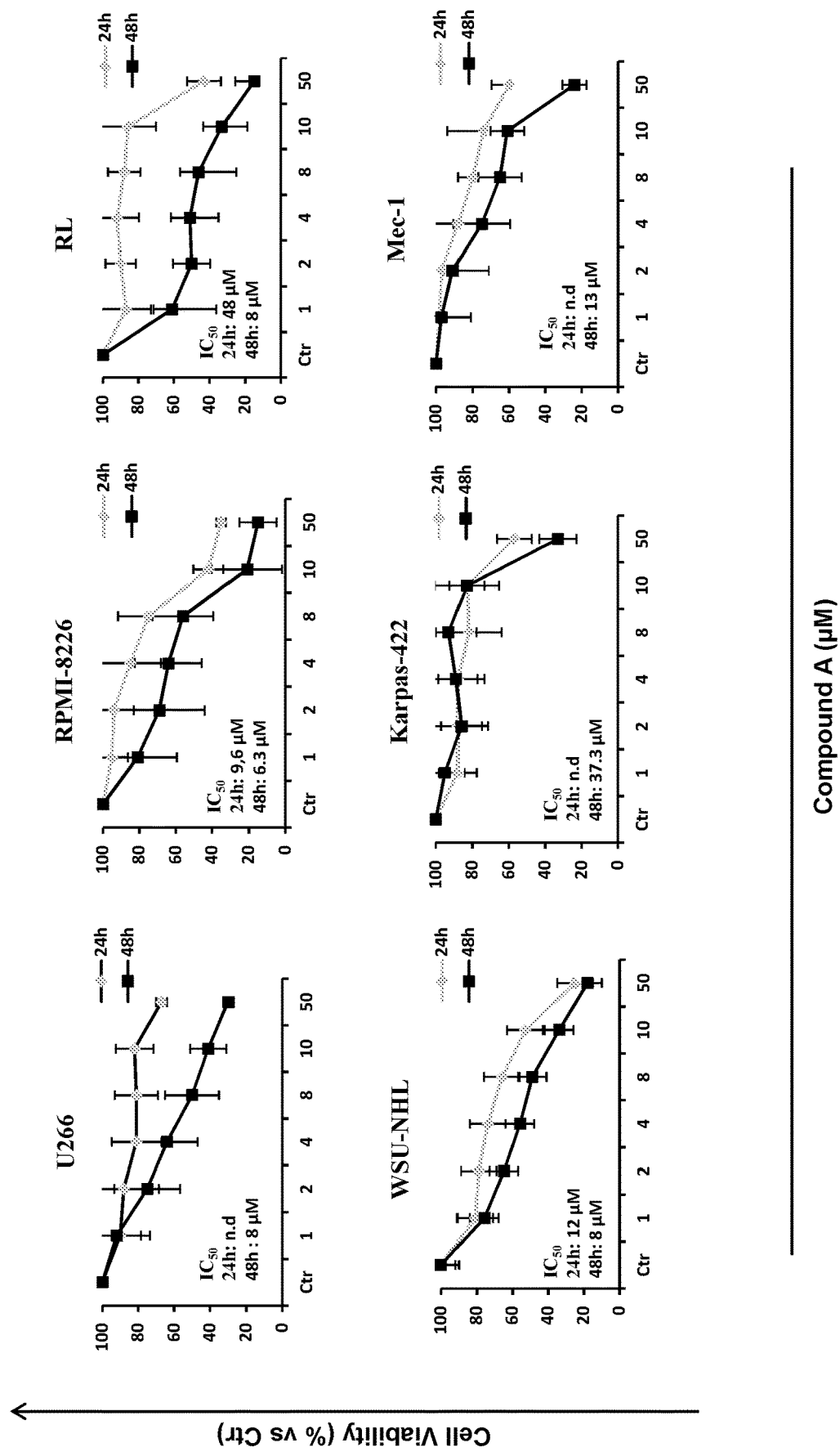
FIG. 2 shows that Compound A decreases cell viability of hematological cancer cell lines. Line graphs show cell viability of 12 different hematological cancer cell lines following treatment with Compound A at either 24 or 48 hours. The $IC_{50}$ of each cell line is noted in the graph. Data are representative of at least three independent experiments and represent the mean±SD.
Figure 2:
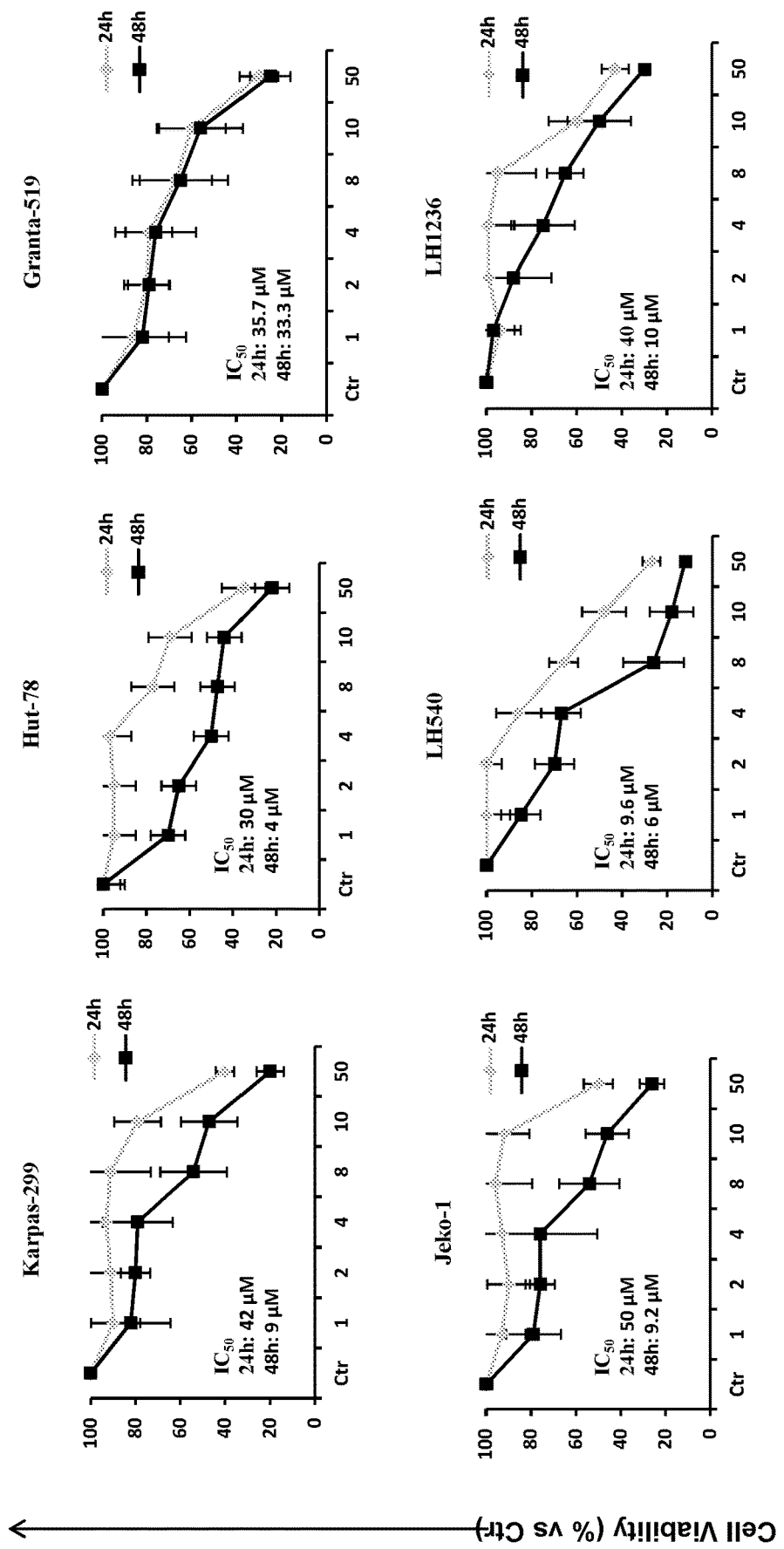

Example 4: Single Agent Therapy with Compound A or Momelotinib Decrease Cell Viability of Hematological Cancer Cell Lines Momelotinib induces dose and time dependent manner growth inhibition in a panel of twelve lymphoid malignant cell lines. Multiple myeloma cells (U266, RPM18266), B-cell lymphoma cells (RL, WSU-NHL, Karpas-422), chronic lymphocytic leukemia cells (MEC-1), mantle cell lymphoma cells (Granta-519, Jeko-1), cutaneous T cell lymphoma cells (Hut-78), anaplastic large cell lymphoma cells (Karpas-299), and Hodgkin lymphoma cells (L-1236, L-540) were treated with a serial dosage of momelotinib (1-10 μM) for 24-48 hours. Momelotinib alone exhibited anti-proliferation potency in cell lines examined with $IC_{50}$ values ranging from 1.8 to 9.6 μM (FIG. 1). The same cell lines were treated for 24-48 hours with Compound A alone, which resulted in time- and dose-dependent inhibition of cell growth with $IC_{50}$ values ranging from 1.51 to 60 μM (FIG. 2).

Figure 3:
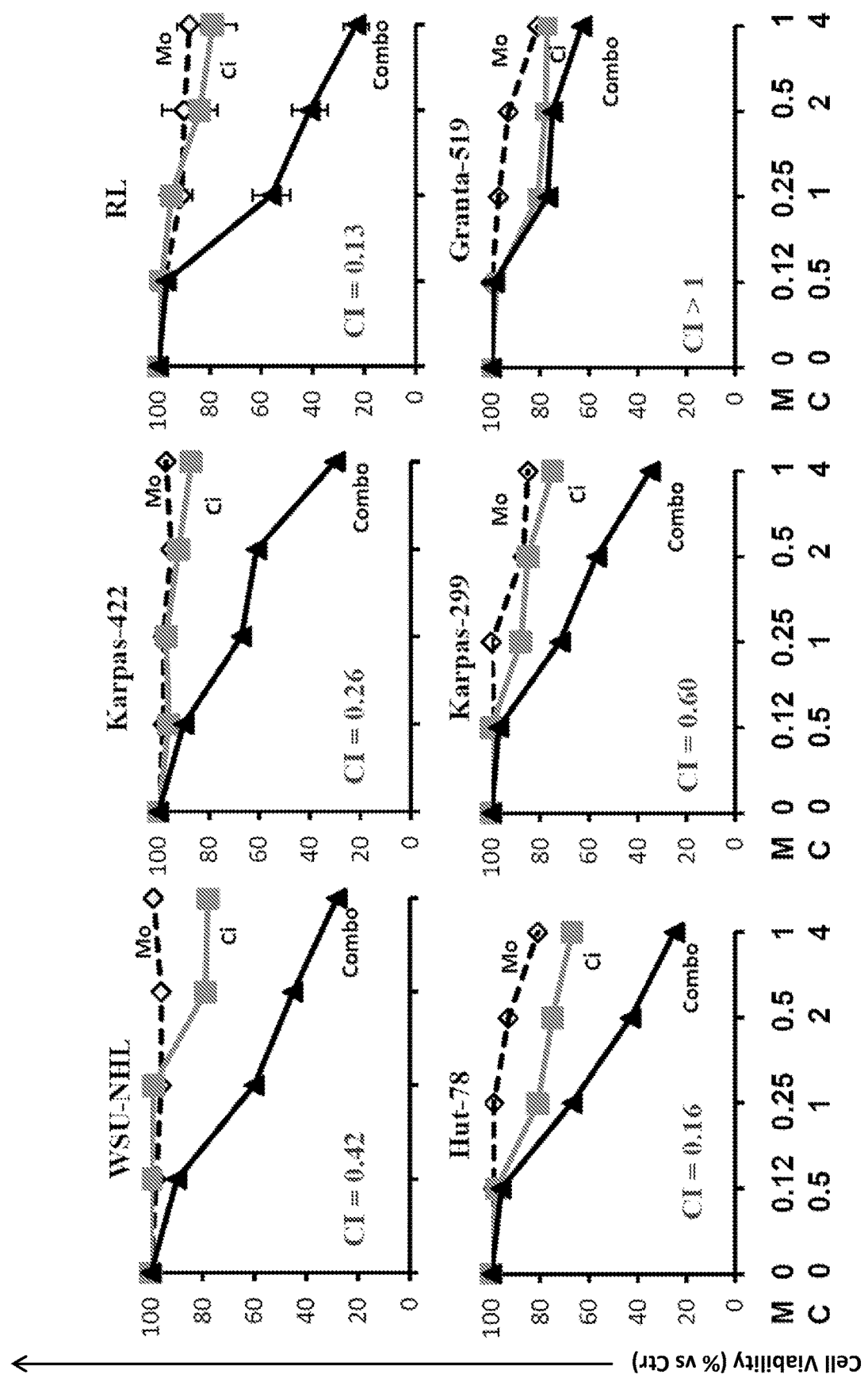
FIG. 3 shows that the combination of Compound A and momelotinib demonstrates synergistic effects in hematological cancer cell lines. A panel of 12 hematological cancer cell lines were treated with varying concentrations of momelotinib (M) (0, 0.12, 0.25, 0.5, and 1 µM) in combination with varying concentrations of Compound A (C) (0, 0.5, 1, 2, and 4 µM). A synergistic interaction was observed with momelotinib (1 µM) and Compound A (4 µM) in WSU-NHL, RL, Karpas-422, Jeko-1, Hut-78, Karpas-299, L-540, RPM18226 and U266 cells with CI (combination index) values <1. Antagonist effects were observed in L-1236, Granta-519 and Me-1 cells with CI>1. The CI values were calculated by Chou Talalay methods.
Figure 3:
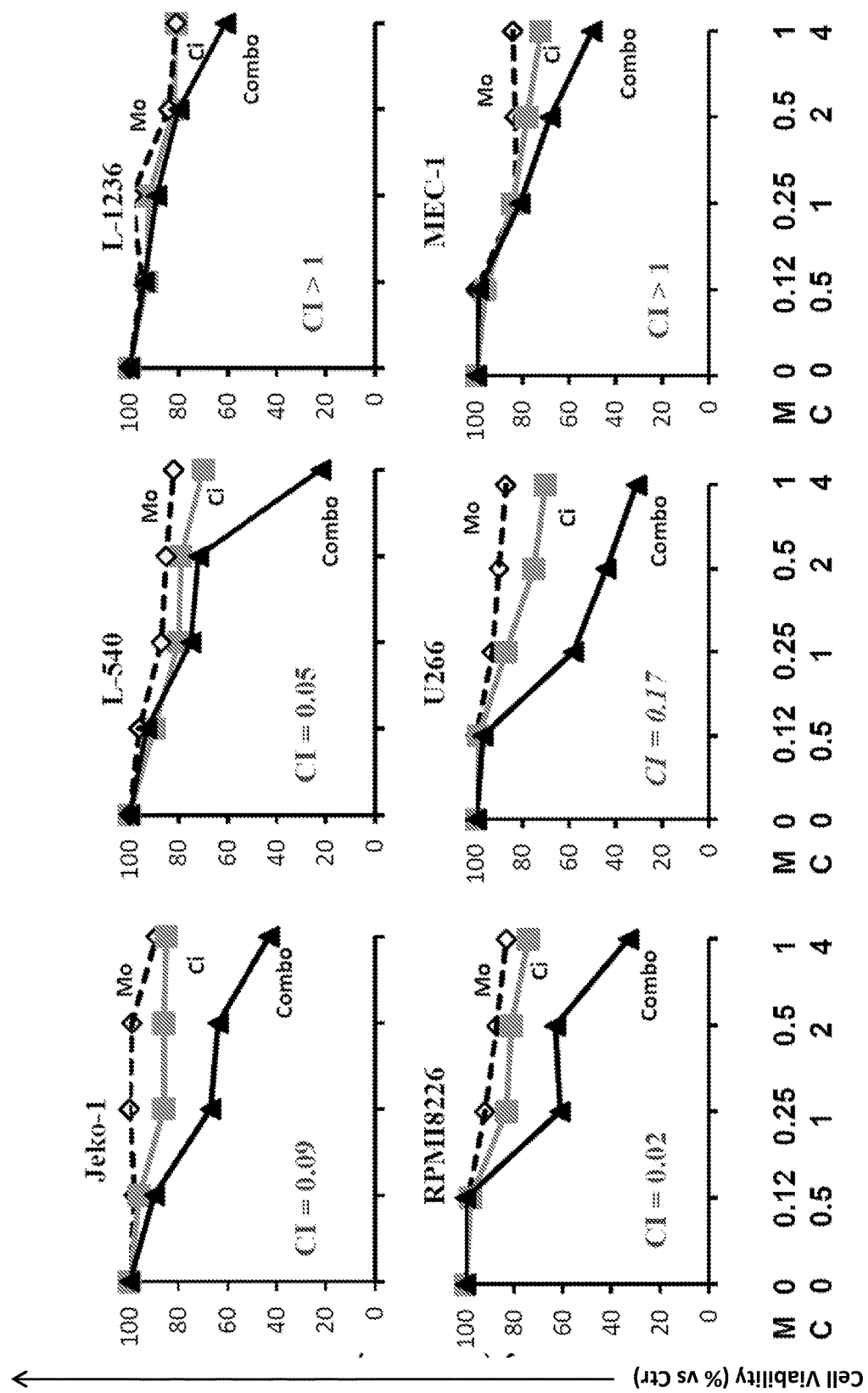

Example 5: Combination Treatment with Compound A and Momelotinib Synergistically Decrease Cell Viability of Hematological Cancer Cell Lines Multiple myeloma cells (U266, RPM18266), B-cell lymphoma cells (RL, WSU-NHL, Karpas-422), chronic lymphocytic leukemia cells (MEC-1), mantle cell lymphoma cells (Granta-519, Jeko-1), cutaneous T cell lymphoma cells (Hut-78), anaplastic large cell lymphoma cells (Karpas-299), and Hodgkin lymphoma cells (L-1236, L-540) were treated with different concentrations of momelotinib (0, 0.25, 0.5, 1 μM) in combination with Compound A (0, 1, 2, 4 μM) and were assayed for cell viability by MTT at 24 hours, before the start of extensive apoptosis. The combination drug treatment induced a cytotoxic effect in most cell lines tested (FIG. 3). A clear synergistic interaction was observed with momelotinib (1 μM) and Compound A (4 μM) in WSU-NHL, RL, Karpas-422, Jeko-1, Hut-78, Karpas-299, L-540, RPM18226 and U266 cells with CI (combination index) values <1 ranging between 0.02 and 0.60. An antagonistic effect was observed in L-1236, Granta-519 and Mec-1 cells with CI>1 (FIG. 3).

Figure 4A:
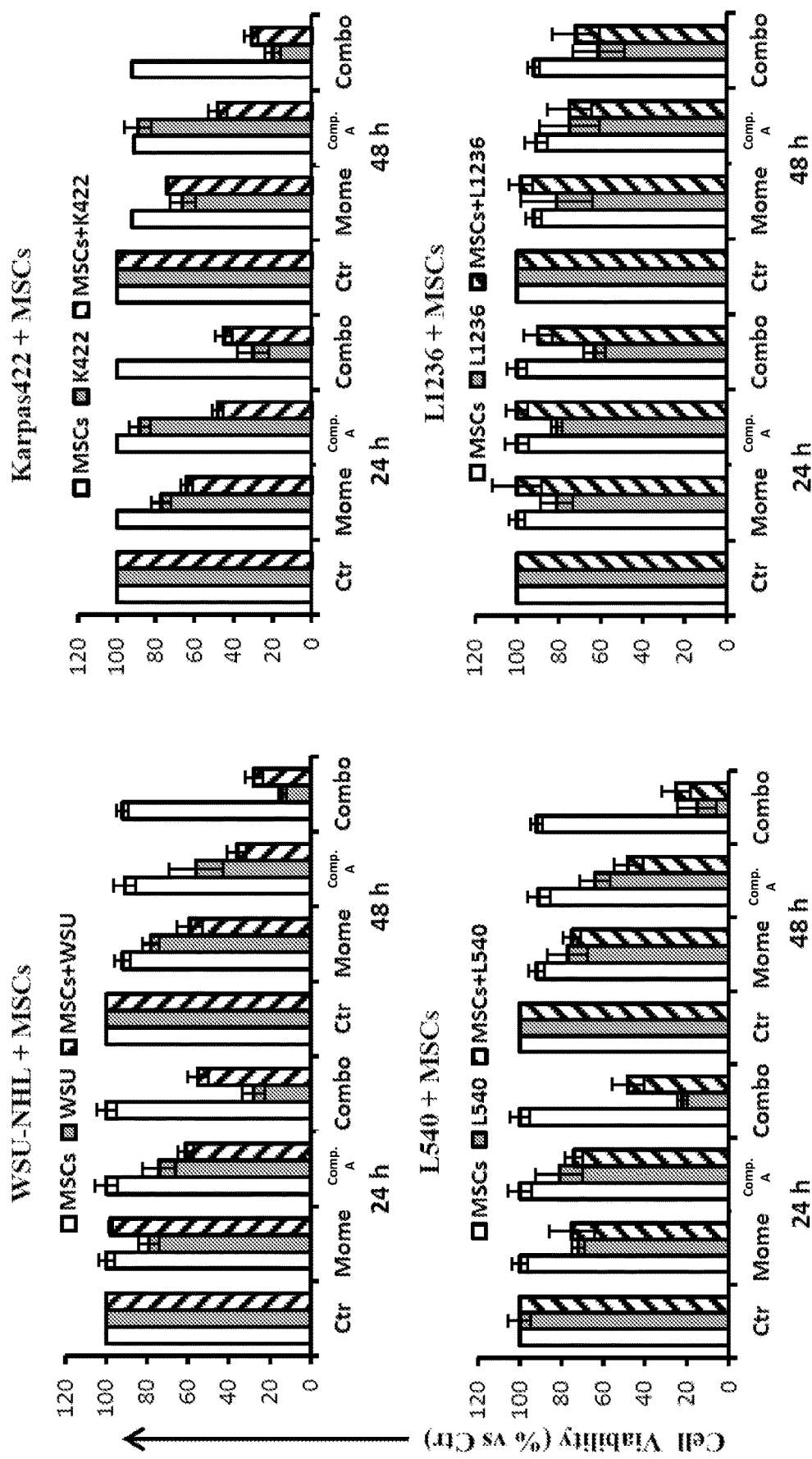
FIG. 4A shows cell viability of three hematological cancer cell lines sensitive to the combination (WSU, K422, L540) and a less sensitive lymphoid cell line (L1236) co-cultured with or without BM-MSCs at 24-48 h.
Figure 4B:
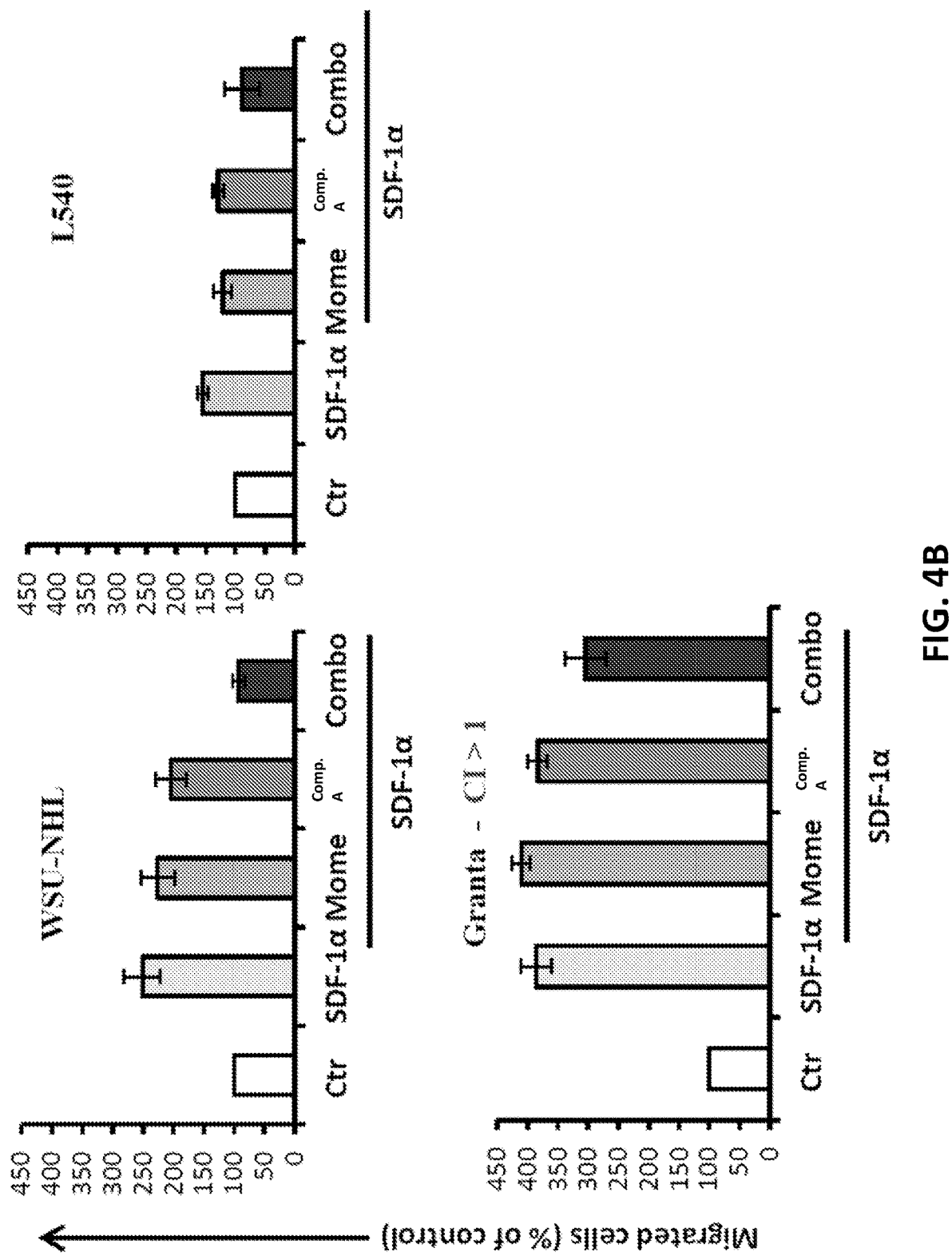
FIG. 4B shows the cell migration of WSU, L450, and Granta cells induced by CXCL12 (chemoattractant known as stromal-cell derived factor-1, SDF-1α), following treatment with momelotinib, Compound A, or the combination of Compound A and momelotinib.
Figure 4C:
FIG. 4C shows the effect of momelotinib, Compound A, or the combination of Compound A and momelotinib on self-renewal by examining clonogenic growth in methylcellulose in five lymphoid cell lines particularly sensitive to the drug combination (WSU, K422, RL, Jeko and L540) and two less sensitive lymphoid cells with CI>1 (Granta and L1236).

Example 6: Effects of Combination Treatment with Compound A and Momelotinib on Cell Cycle Progression and Apoptosis in Hematological Cancer Cell Lines From the panel of 12 hematological cancer cell lines tested in Example 5, five cell lines which were particularly sensitive to the drug combination (WSU-NHL, Karpas422, RL, Jeko1, L-540) and two cell lines that showed a CI>1 (L-1236, Granta-519) were chosen for further analysis. The combination of momelotinib and Compound A suppressed cell viability of lymphoid cells even when co-cultured with bone marrow mesenchymal stromal cells (FIG. 4A), inhibited the migration induced by CXCL12 (chemoattractant known as stromal-cell derived factor-1, SDF-1α) (FIG. 4B), and reduced clonogenic survival (FIG. 4C).

Figure 5A:
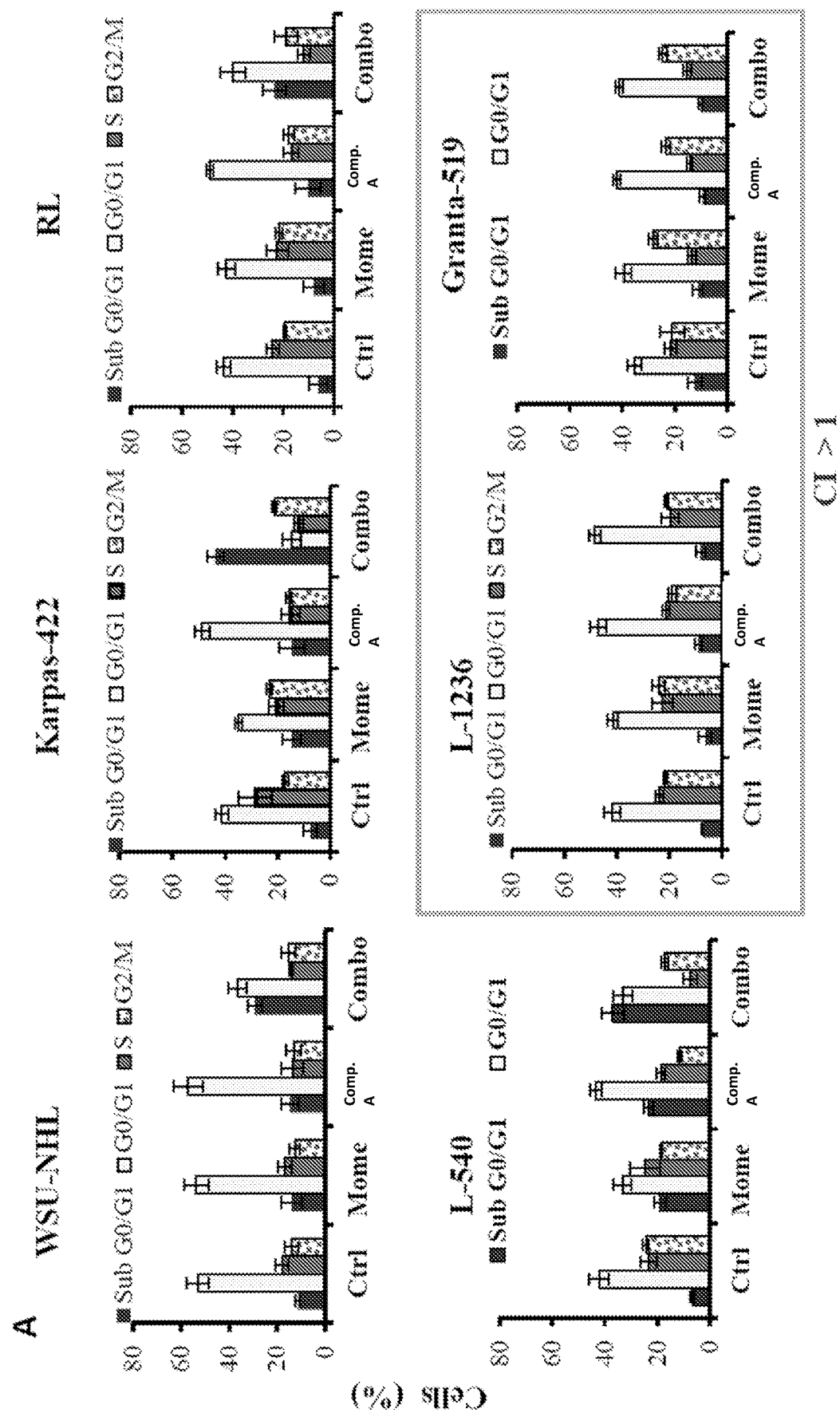
FIG. 5A shows the cell cycle distribution (%) of four cell lines sensitive to the combination (WSU-NHL, Karpas422, RL and L540) and two lines with CI>1 (Granta-519 and L-1236) after 24 hours of treatment.
Figure 5B:
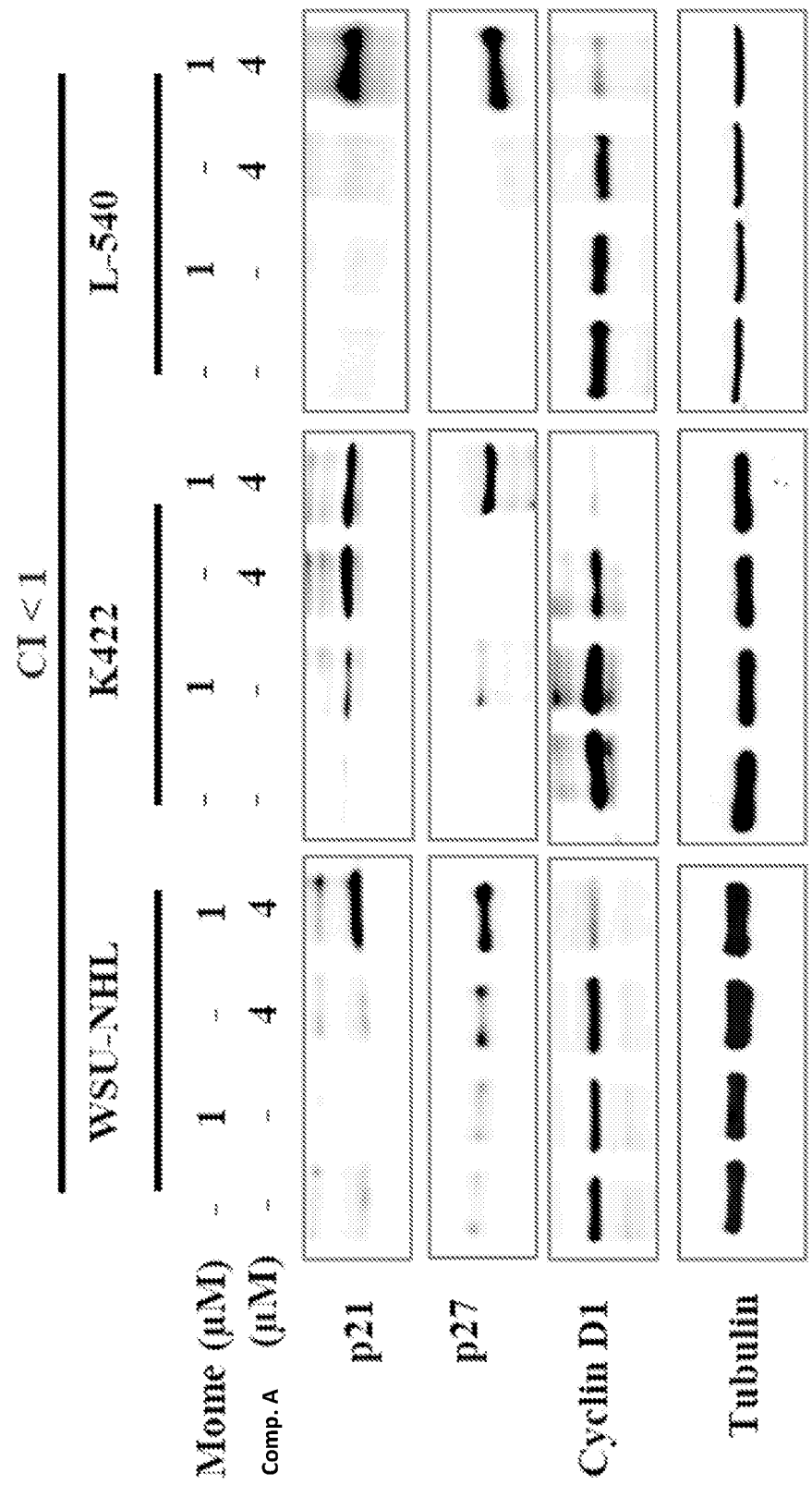
FIG. 5B shows representative western blots of cellular extracts from WSU-NHL, Karpas-422, and L540 treated with the drugs alone and in combination for 24 h. Tubulin was used to normalize protein loading.
Figure 6B:
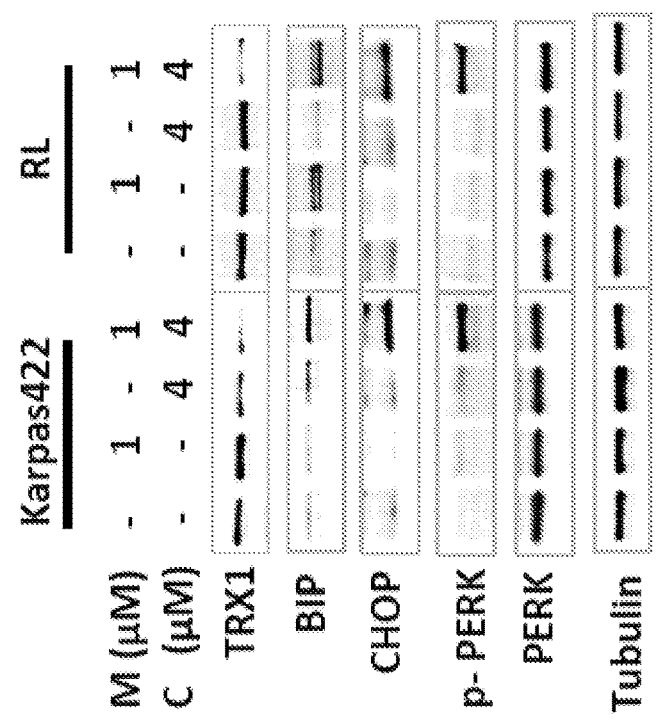
FIG. 6B shows representative western blots of cellular extracts from Karpas-422, and RL cells treated with the drugs alone and in combination for 24 h. Tubulin was used to normalize protein loading.
Figure 6A:
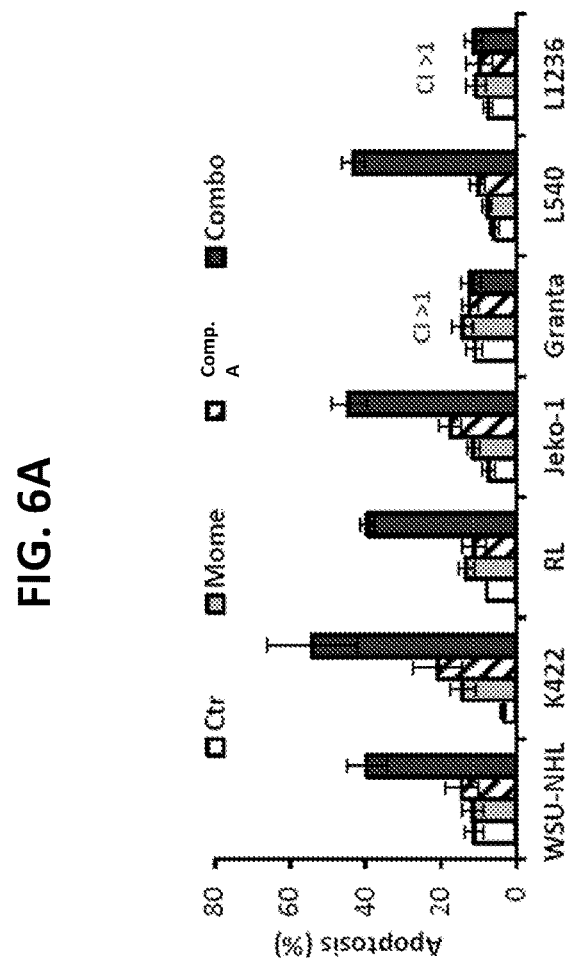
FIG. 6A shows the percentages of apoptotic cells of lymphoma cells after 24 hours of exposure to the drug combination.
Figure 6C:
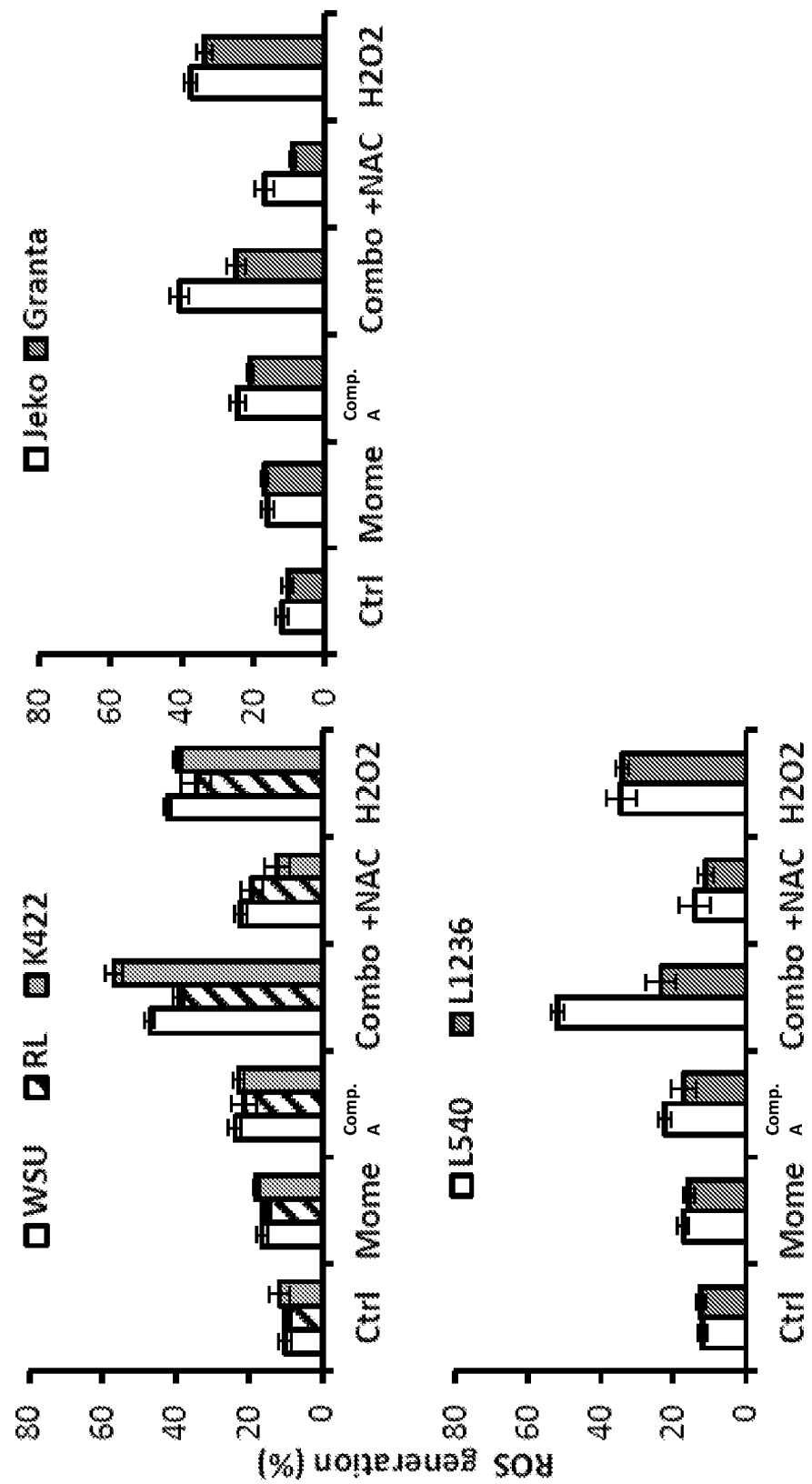
FIG. 6C shows the percentage of cells with increased ROS level treated with momelotinib, Compound A, or the combination of Compound A and momelotinib compared with the control cells. H22 was used as a positive control.

Further, while in L-1236 and Granta-519 cell lines, the combination treatment of Compound A and momelotinib had minimal or no cytotoxic effect, in WSU-NHL, RL, and L-540 cells, in which the combination treatment showed a synergistic effect, an increase of cells in sub-G0/G1 phase and a reduction in S phase after 24 hours was observed (FIG. 5A). Further analysis of these cells showed that the combination of Compound A and momelotinib caused an increase of p21 and p27 proteins and in parallel the level of cyclin D1 decreased (FIG. 5). In sensitive hematological cancer cell lines (WSU-NHL, Karpas422, RL, Jeko1, L-540), compared with each single agent, the percentage of apoptotic cells ranged from 39 to 54% upon treatment with the combination of Compound A and momelotinib (FIG. 6A). The induction of apoptosis was correlated with a decrease of Trx1 expression and with increased expression of ER stress sensors (BIP, CHOP, PERK) (FIG. 6B). The Trx system is an antioxidant system integral to maintaining the intracellular redox state. Combined therapy with Compound A and momelotinib induced ER stress and ROS generation, which in turn triggered apoptosis (FIG. 6C). The combination of Compound A and momelotinib induced a significant increase in ROS-positive cells from 39 to 56% and co-administration of the antioxidant NAC, a ROS scavenger, reduced the generation of ROS (FIG. 6C).

Figure 6D:
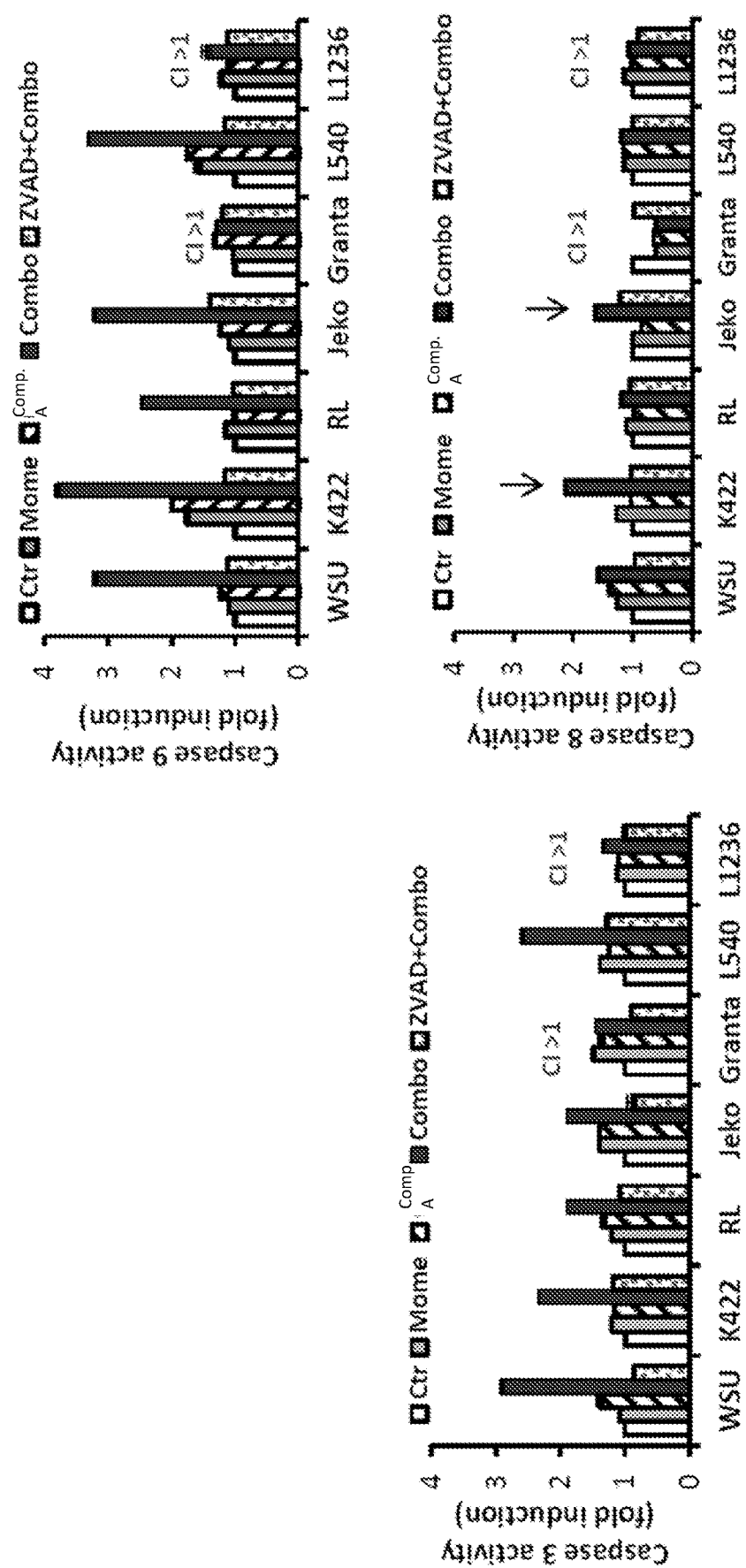
FIG. 6D shows caspase 9 caspase 3, and caspase 8 protease assays for the determination of caspase proteolytic activity in lysates of lymphoma cells after treatment.
Figure 7A:
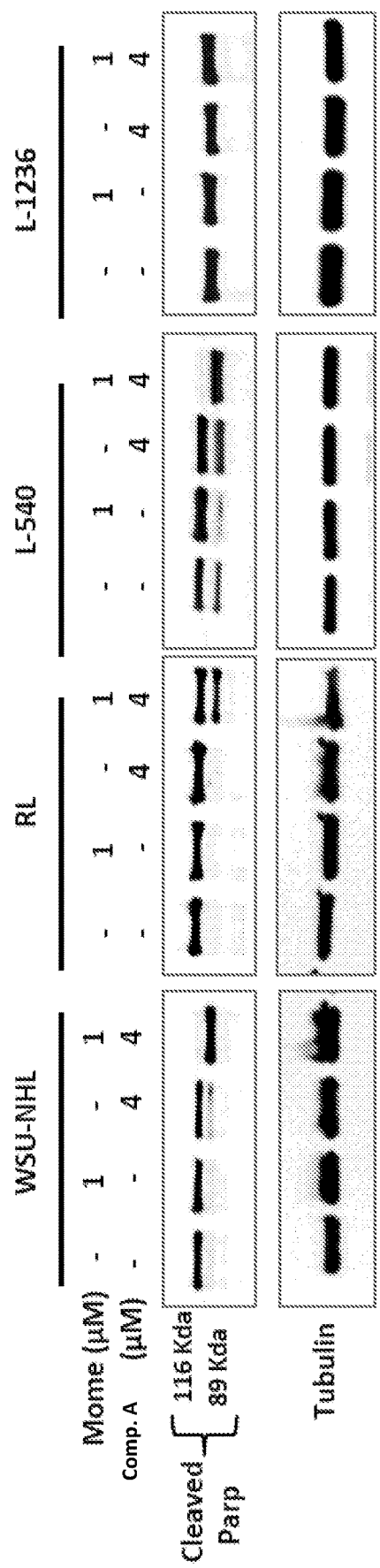
FIG. 7A shows western blots of cellular extracts from lymphoma cells treated with the drugs alone or in combination at the indicated doses for 24 hours. Whole-cell lysates were subjected to western blotting using the indicated Abs. Tubulin was used to normalize protein loading.
Figure 7C:
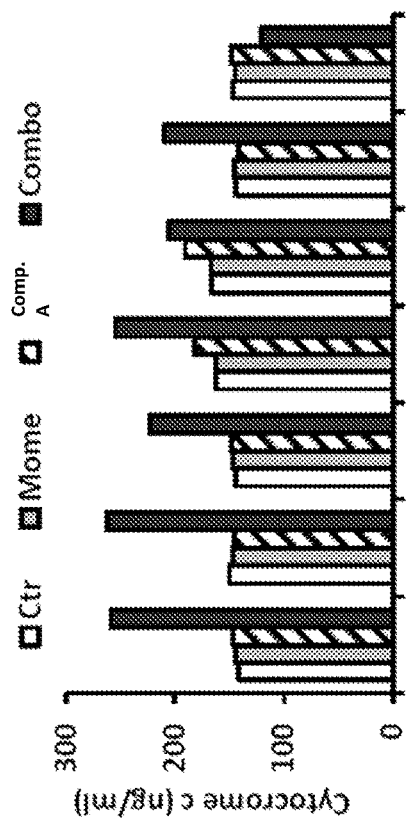
FIG. 7 shows the effects of Compound A and momelotinib on cytotoxicity.
FIG. 7B shows that the drug combination exhibited a strong cytotoxicity, evidenced by reduction of mitochondrial depolarization and by Cyt-C release (FIG. 7C).
FIG. 7D shows intracellular ATP levels after 24 hours with drugs alone and in combination.
FIG. 7E shows lactate levels after treatment with drugs alone and in combination
Figure 7B:
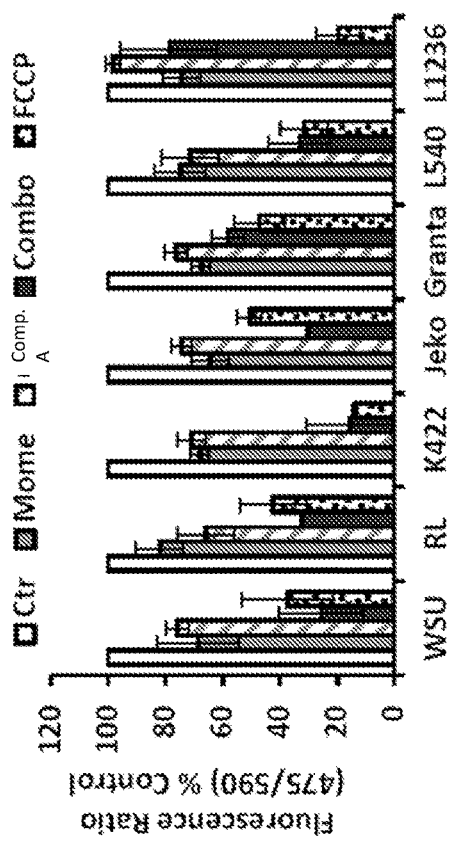
Figure 7E:
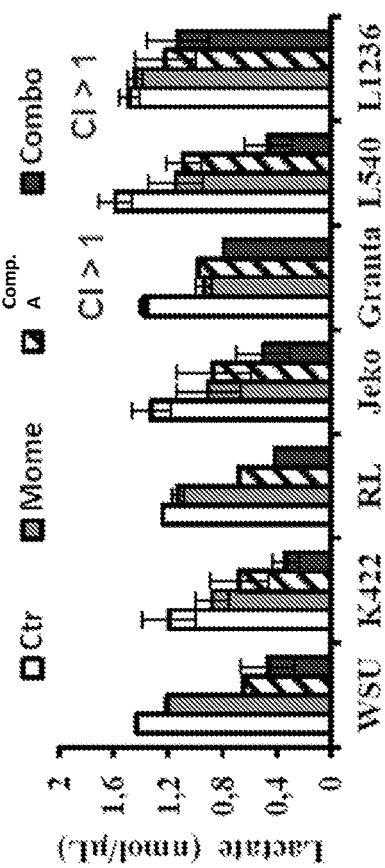
Figure 7D:
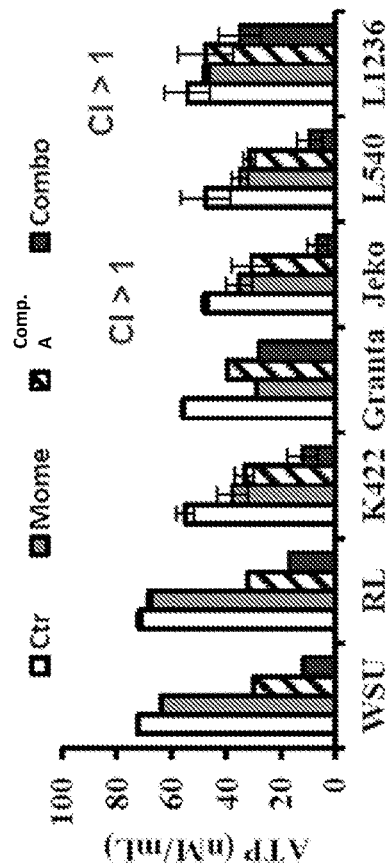

The apoptosis induced by the drug combination was executed mainly via the mitochondrial apoptotic pathway (intrinsic apoptotic pathway) as demonstrated by upregulation of caspase-9, which was especially evident in WSU-NHL, Karpas422, Jeko, and L-540 with a fold induction of 3.2 and 3.8 compared to the control sample (FIG. 6D). The apoptosis induced was associated with activation of caspase-3 (FIG. 6D), which are prevented by the ZVAD-fmk broad caspase inhibitor (FIG. 6D). No caspase-8 activation (extrinsic apoptotic pathway) was induced within 24 hours of combination treatment (FIG. 6D). After 24 hours of combination treatment with Compound A and momelotinib, the extrinsic apoptotic pathway was active in Karpas422 and Jeko1 cells as evaluated by upregulation of caspase-8 but not in WSU-NHL, RL and L540 cells (FIG. 6D). The combination treated cells also exhibited a strong cytotoxicity evidenced by PARP cleavage (FIG. 7A), the hallmark of apoptosis, and by reduction of mitochondrial depolarization (FIG. 7B), Cyt-C release from the mitochondria (FIG. 7C), depletion of ATP (FIG. 7D), and lactate levels (FIG. 7E).

Figure 8A:
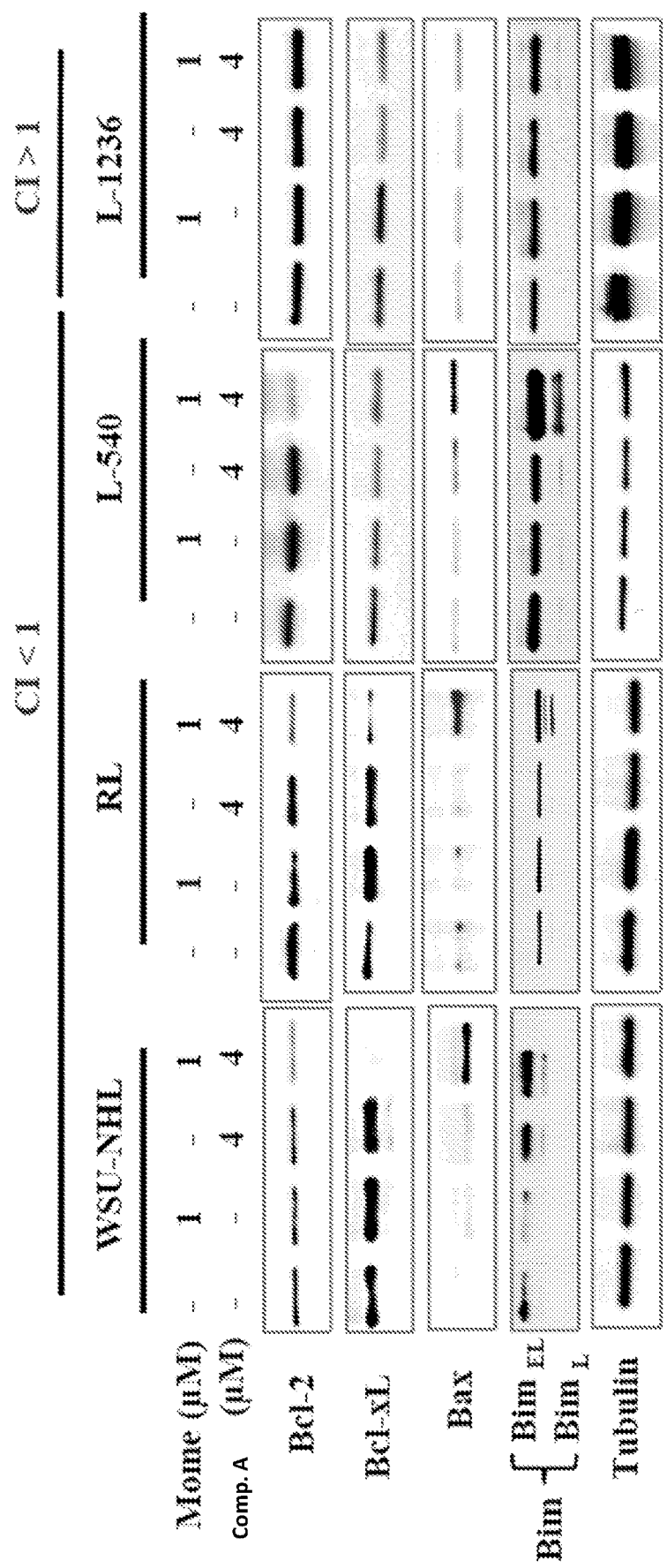
FIG. 8A shows western blots of Bcl-2 family proteins. Whole-cell lysates were subjected to western blotting using the indicated Abs. Tubulin was used to normalize protein loading.

Example 7: Combination Treatment with Compound A and Momelotinib Affects Expression of JAK/STAT and BCL-2 Family Proteins in Hematological Cancer Cell Lines The combination treatment of Compound A and momelotinib increased the expression of pro-apoptotic proteins Bax and Bim (FIG. 8A) and downregulated the expression of key anti-apoptotic regulators, Bcl2 and Bcl-xL (FIG. 8A) in WSU-NHL, RL, and L-540 cells. The downregulation of Bcl2 and Bcl-xL could explain the proapoptotic effect of the combination of Compound A and momelotinib.

Figure 8B:
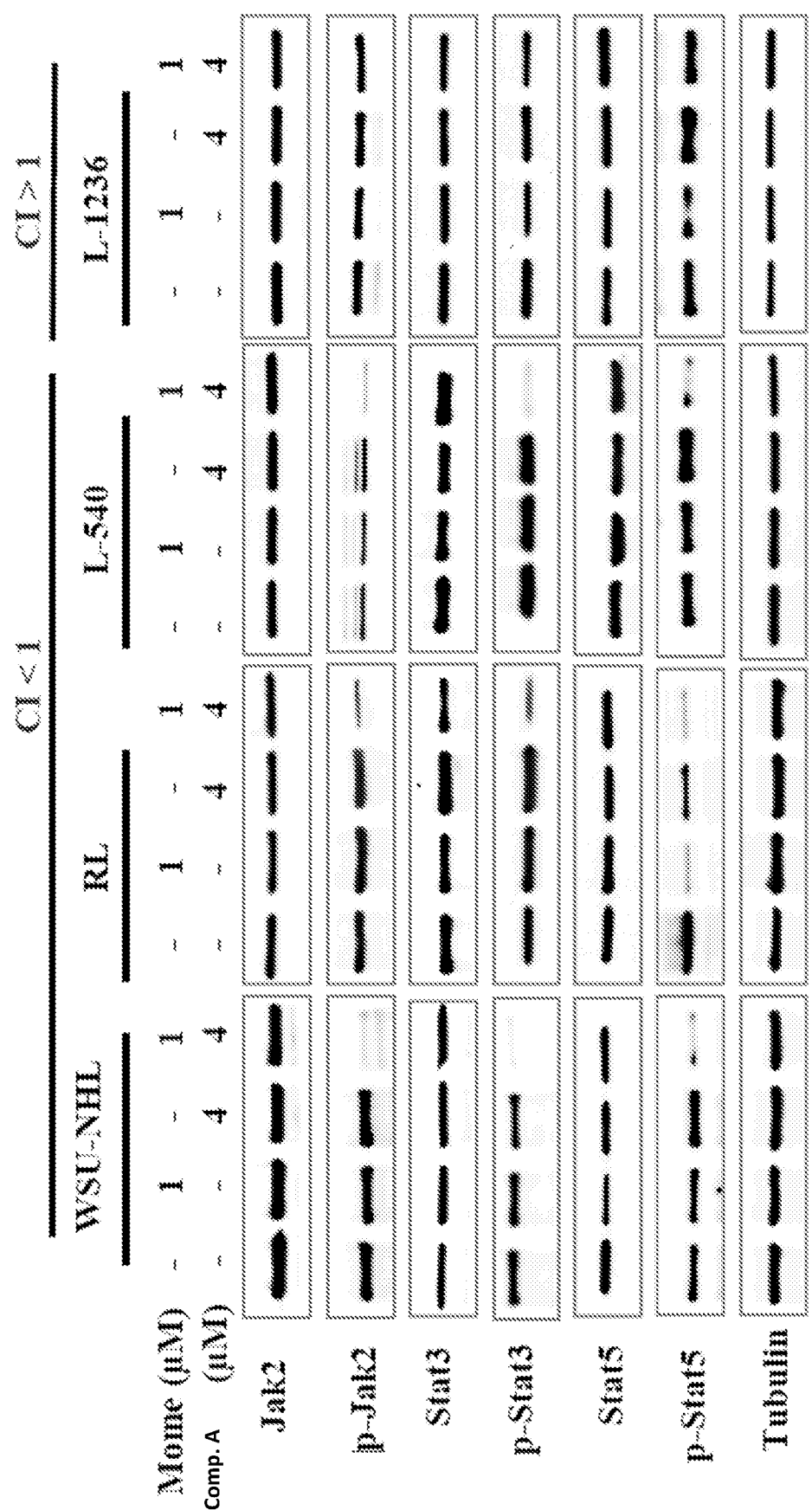
FIG. 8B shows that the drug combination mediated the down regulation of JAK2/STAT proteins. Whole-cell lysates were subjected to western blotting using the indicated Abs. Tubulin was used to normalize protein loading.
Figure 8C:
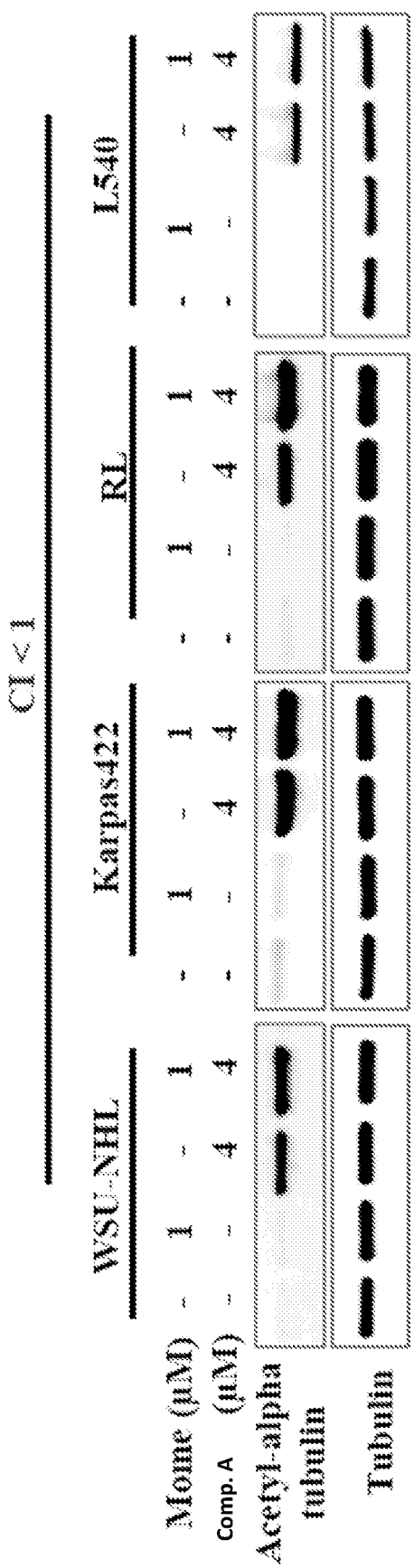
FIG. 8C shows western blot analysis of the acetylation of α-tubulin in lymphoma cells treated with momelotinib, Compound A, or the combination of Compound A and momelotinib.

The combination treatment with momelotinib and Compound A leads JAK2/STAT3 pathway inactivation. The momelotinib/Compound A combination inhibited the phosphorylation of JAK2 and its downstream mediators, including STAT3 and STAT5 (FIG. 8B). Further, the exposure of the cells to Compound A induced the acetylation of α-tubulin in lymphoma cells, the extent of which was not further modified by momelotinib treatment (FIG. 8C).

Example 8: Materials and Methods

Reagents

Momelotinib and Compound A were dissolved in DMSO and stored at −20° C. until use. In all experiments, the final concentration of DMSO which was used as vehicle control did not exceed 0.01%.

Screening

Momelotinib and Compound A alone and in combination were tested in 12 hematological cancer cell lines: B-cell lymphomas (WSU-NHL, RL, Karpas-422), mantle cell lymphoma (Granta-519, Jeko-1), cutaneous T cell lymphoma (Hut-78), anaplastic large cell lymphoma (Karpas-299), Hodgkin lymphoma (L-1236, L-540), multiple myeloma (U266, RPM18266) and chronic lymphocytic leukemia (MEC-1). With the exception of GRANTA-519, hematological cancer cell lines were cultured in RPMI-1640 supplemented with 10% fetal bovine serum (FBS), 2 mM glutamine, and 100 U/mL penicillin and streptomycin. For Granta-519 cells, DMEM was used in place of RPMI-1640.
Viability Assay Cell viability was evaluated by MTT colorimetric assay following the manufacturer's instructions. Hematological cancer cell lines were incubated in triplicate with increasing concentrations of momelotinib (1-10 µM) and Compound A (1-100 µM) as single agents for 24-48 hours to identify the $IC_{50}$ values of each drug.
Combination Treatment For assessment of drug combination effect, serial dilutions of the two agents were assessed using concentrations lower than the $IC_{50}$. Hematological cancer cell lines were cultured with fixed doses of momelotinib (0, 0.25, 0.5, 1 µM) and Compound A (0, 1, 2, 4 µM) for 24 hours and the interaction was evaluated using the Chou-Talalay method. The effectiveness of the drugs and their combinations used in the present study were analysed using Calcusyn Software. The combination index (CI) and isobologram plot were calculated according to the Chou-Talalay method. Synergism, additivity, or antagonism were quantified by determining the combination index (CI) calculated by the Chou-Talalay equation. CI<1, CI=1, and CI>1 indicate synergistic, additive, and antagonistic effects, respectively. All in vitro experiments were performed in triplicate, and repeated at least three times.
Cell Cycle Distribution Cell cycle was determined by flow cytometry. Malignant cell lines were cultured for 24-48 hours with momelotinib (1 µM) and Compound A (4 µM) either alone or in combination. The cells were harvested, washed with ice-cold PBS, and fixed overnight with ice-cold 70% ethanol at 4° C. The fixed cells were washed with PBS, resuspended in citrate buffer, and stained with PI containing RNase A for 30 minutes at 37° C.
Assessment of Apoptosis Apoptosis was quantified using the Annexin V-FITC and propidium iodide (PI) binding assay, following the manufacturer's instructions and analyzed by flow cytometry. Apoptotic cells were designated as Annexin $V^+/PI^-$ and Annexin $V^+/PI^+$, showing early and late apoptosis, respectively.
Assessment of Enzymatic Activity of Caspases 3, 8, and -9

Caspase 3, 8, and 9 activity was measured using colorimetric assay following the manufacturer's instructions.
Assessment of ATP Levels and Mitochondrial Membrane Potential ATP levels and Mitochondrial Membrane Potential (Δψm) were evaluated by fluorometric assay following the manufacturer's instructions.
Assessment of Lactate and Cytochrome C Lactate levels and Cyt-C were evaluated by colorimetric assay following the manufacturer's instructions.
Protein Analysis by Western Blot.

Cell pellets were resuspended in cold lysis buffer following the manufacturer's instructions. Cell lysates (50-100 µg of protein) were loaded onto pre-cast 4-20% (w/v) Miniprotean TGX Precast Gels, subjected to electrophoresis, and electrotransferred onto nitrocellulose membranes. The membranes were incubated overnight at 4° C. and were probed with antibodies against the following protein: $Bcl_2$, Bcl-xL, Bax, Bim, PARP and caspase 8, JAK2, STAT3, STAT5. Images were acquired and analyzed using Image Lab Software v.3.0.

INCORPORATION BY REFERENCE

The contents of all references (including literature references, issued patents, published patent applications, and co-pending patent applications) cited throughout this application are hereby expressly incorporated herein in their entireties. Unless otherwise defined, all technical and scientific terms used herein are accorded the meaning commonly known to one with ordinary skill in the art.

EQUIVALENTS

Those skilled in the art will recognize, or be able to ascertain using no more than routine experimentation, many equivalents of the specific embodiments of the disclosure described herein. Such equivalents are intended to be encompassed by the following claims.

What is claimed is:

1. A method of treating hematological cancer in a subject in need thereof, comprising administering to the subject a therapeutically effective amount of:

a) a compound of Formula I

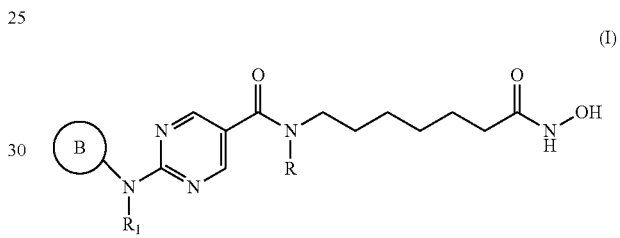

or a pharmaceutically acceptable salt thereof, wherein ring B is aryl or heteroaryl;

$R_1$ is aryl or heteroaryl, each of which may be optionally substituted by OH, halo, or $C_{1-6}$-alkyl;

and

R is H or $C_{1-6}$-alkyl; and b) a JAK1/2 inhibitor, wherein the JAK1/2 inhibitor is momelotinib, or a pharmaceutically acceptable salt thereof.

2. The method of claim 1, wherein the compound of Formula I is Compound A

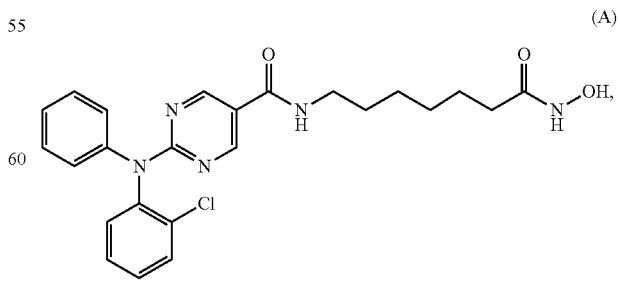

or a pharmaceutically acceptable salt thereof.

3. The method of claim 1, wherein the compound of Formula I is Compound B

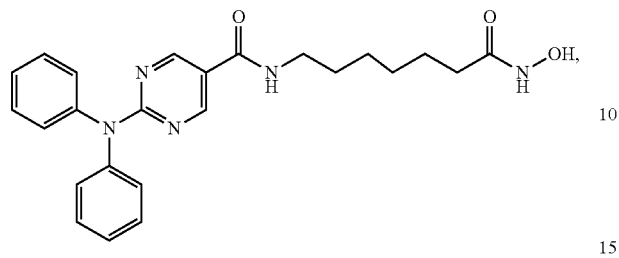

(B)

or a pharmaceutically acceptable salt thereof.

4. The method of claim 1, wherein the compound of Formula I and the JAK1/2 inhibitor are formulated together as a single formulation.

5. The method of claim 1, wherein the compound of Formula I and the JAK1/2 inhibitor are each formulated as separate formulations.

6. The method of claim 1, wherein the compound of Formula I and the JAK1/2 inhibitor are administered at substantially the same time.

7. The method of claim 1, wherein the compound of Formula I and the JAK1/2 inhibitor are administered at different times.

8. The method of claim 1, wherein the hematological cancer is selected from the group consisting of leukemia, lymphoma, and multiple myeloma.

* * * * *